(12) United States Patent
Roisen et al.

US007838292B1

(10) Patent No.: US 7,838,292 B1
(45) Date of Patent: Nov. 23, 2010

(54) METHODS FOR OBTAINING ADULT HUMAN OLFACTORY PROGENITOR CELLS

(75) Inventors: Fred J. Roisen, Prospect, KY (US); Kathleen M. Klueber, Louisville, KY (US); Chengliang Lu, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 890 days.

(21) Appl. No.: 10/112,658

(22) Filed: Mar. 29, 2002

Related U.S. Application Data

(60) Provisional application No. 60/279,933, filed on Mar. 29, 2001, provisional application No. 60/352,906, filed on Jan. 28, 2002.

(51) Int. Cl.
*C12N 5/02* (2006.01)
*C12N 5/0797* (2010.01)
*A61K 35/30* (2006.01)

(52) U.S. Cl. .................. 435/377; 424/570; 424/93.7; 435/347; 435/325; 435/368

(58) Field of Classification Search ............... None
See application file for complete search history.

(56) References Cited

U.S. PATENT DOCUMENTS

| | | | |
|---|---|---|---|
| 4,863,899 A | 9/1989 | Todaro | |
| 5,196,315 A | 3/1993 | Ronnett et al. | |
| 5,217,893 A | 6/1993 | Ronnett et al. | |
| 5,223,409 A | 6/1993 | Ladner et al. | |
| 5,240,912 A | 8/1993 | Todaro | |
| 5,308,763 A | 5/1994 | Ronnett et al. | |
| 5,318,907 A | 6/1994 | Ronnett et al. | |
| 5,411,883 A * | 5/1995 | Boss et al. ............ | 435/29 |
| 5,459,039 A | 10/1995 | Modrich et al. | |
| 5,750,103 A | 5/1998 | Cherksey | |
| 5,750,376 A * | 5/1998 | Weiss et al. ........... | 435/69.52 |
| 5,753,506 A | 5/1998 | Johe | |
| 5,766,948 A | 6/1998 | Gage et al. | |
| 5,830,651 A | 11/1998 | Cauley et al. | |
| 5,851,832 A | 12/1998 | Weiss et al. | |
| 5,869,266 A * | 2/1999 | Wolozin et al. ......... | 435/7.21 |
| 5,958,767 A | 9/1999 | Snyder et al. | |
| 5,968,829 A | 10/1999 | Carpenter | |
| 5,980,885 A * | 11/1999 | Weiss et al. ........... | 424/93.21 |
| 5,981,165 A | 11/1999 | Weiss et al. | |
| 6,001,654 A | 12/1999 | Anderson et al. | |
| 6,020,197 A | 2/2000 | Gage et al. | |
| 6,040,180 A | 3/2000 | Johe | |
| 6,045,807 A | 4/2000 | Gage et al. | |
| 6,071,889 A | 6/2000 | Weiss et al. | |
| 6,093,531 A | 7/2000 | Bjornson et al. | |
| 6,103,530 A | 8/2000 | Carpenter | |
| 6,117,675 A | 9/2000 | van der Kooy et al. ..... | 435/354 |
| 6,129,911 A | 10/2000 | Faris ................. | 424/93.7 |
| 6,162,428 A | 12/2000 | Snable | |
| 6,165,783 A | 12/2000 | Weiss et al. | |
| 6,197,585 B1 | 3/2001 | Stringer | |
| 6,200,806 B1 | 3/2001 | Thomson .............. | 435/366 |
| 6,238,922 B1 | 5/2001 | Uchida | |
| 6,251,669 B1 | 6/2001 | Luskin | |
| 6,265,175 B1 | 7/2001 | Gage et al. | |
| 6,284,539 B1 | 9/2001 | Bowen et al. | |
| 6,294,346 B1 | 9/2001 | Weiss et al. | |
| 6,368,854 B2 | 4/2002 | Weiss et al. | |
| 6,399,369 B1 | 6/2002 | Weiss et al. | |
| 6,465,248 B1 | 10/2002 | Commissiong | |
| 6,468,794 B1 | 10/2002 | Uchida et al. | |
| 6,486,122 B1 | 11/2002 | Twardzik et al. | |
| 6,497,872 B1 | 12/2002 | Weiss et al. | |
| 6,498,018 B1 | 12/2002 | Carpenter | |
| 6,528,306 B1 | 3/2003 | Snyder et al. | |
| 6,541,255 B1 | 4/2003 | Snyder et al. | |
| 6,638,501 B1 | 10/2003 | Bjornson et al. | |
| 6,638,763 B1 | 10/2003 | Steindler et al. | |
| 6,677,307 B2 | 1/2004 | Twardzik et al. | |
| 6,680,198 B1 | 1/2004 | Snyder et al. | |
| 6,764,683 B1 | 7/2004 | Twardzik et al. | |
| 6,777,233 B2 | 8/2004 | Carpenter | |
| 6,787,355 B1 | 9/2004 | Miller et al. | |
| 6,815,418 B2 | 11/2004 | Twardzik et al. | |
| 6,844,312 B2 | 1/2005 | Weiss et al. | |
| 6,878,543 B1 | 4/2005 | Wahlberg et al. | |
| 6,969,608 B1 | 11/2005 | Miller et al. | |
| 7,033,995 B2 | 4/2006 | Weiss et al. | |
| 7,048,934 B2 | 5/2006 | Thompson et al. | |
| 7,049,141 B1 | 5/2006 | Uchida | |
| 7,101,709 B2 | 9/2006 | Weiss et al. | |

(Continued)

FOREIGN PATENT DOCUMENTS

CA 2213780 2/1998

(Continued)

OTHER PUBLICATIONS

Lanza 1993. Laryngoscope 103:815-819.*
Kleinman 1998. Current Protocols in Cell Biology 2.3.1-2.3.6).*
Kalyani 1997 (Developmental Biology 186:202-223).*
Piper 2000 (J Neurophysiol 84:534-548).*
Roisen, F.J., et al., "Adult human olfactory stem cells"., Brain Research, vol. 890, pp. 11-22, (2001).
Winstead, W., et al., "Endoscopic biopsy of human olfactory epithelium as a source of progenitor cells"., American Journal of Rhinology, vol. 19, No. 1, pp. 83-90, (2005).
About.com Guide to Rare/Orphan Diseases, "Debate Over Use of Embryonic Stem Cells", by Mary Kugler, MSN, dated Apr. 3, 2001.

(Continued)

*Primary Examiner*—Daniel E Kolker
(74) *Attorney, Agent, or Firm*—Fish & Richardson P.C.

(57) ABSTRACT

An isolated human olfactory stem cell can be prepared by culturing human tissue from olfactory neuroepithelium to form neurospheres.

14 Claims, 5 Drawing Sheets

U.S. PATENT DOCUMENTS

| | | | |
|---|---|---|---|
| 7,105,342 | B2 | 9/2006 | Weiss et al. |
| 7,115,418 | B2 | 10/2006 | Weiss et al. |
| 7,132,286 | B2 | 11/2006 | Laeng et al. |
| 7,166,277 | B1 | 1/2007 | Weiss et al. |
| 7,204,979 | B2 | 4/2007 | Bjornson et al. |
| 7,211,404 | B2 | 5/2007 | Lagasse et al. |
| 7,214,372 | B2 | 5/2007 | Rao et al. |
| 7,303,912 | B2 | 12/2007 | Wahlberg et al. |
| 7,329,645 | B2 | 2/2008 | Twardzik et al. |
| 7,361,505 | B1 | 4/2008 | Weiss et al. |
| 7,368,115 | B2 | 5/2008 | Ohta et al. |
| 7,393,830 | B2 | 7/2008 | Shingo et al. |
| 7,534,765 | B2 | 5/2009 | Gregg et al. |
| 7,544,509 | B2 | 6/2009 | Toma et al. |
| 7,544,511 | B2 | 6/2009 | Yang et al. |
| 7,560,553 | B1 | 7/2009 | Kelleher-Andersson et al. |
| 7,598,082 | B1 | 10/2009 | Brandon et al. |
| 7,604,993 | B2 | 10/2009 | Thompson et al. |
| 7,629,169 | B2 | 12/2009 | Weiss et al. |
| 7,632,681 | B2 | 12/2009 | Kopyov |
| 7,651,853 | B2 | 1/2010 | Wahlberg et al. |
| 7,691,629 | B2 | 4/2010 | Johe et al. |
| 7,704,737 | B2 | 4/2010 | Weiss |
| 7,732,201 | B2 | 6/2010 | Gage et al. |
| 2002/0016002 | A1 | 2/2002 | Toma et al. |
| 2002/0123143 | A1 | 9/2002 | Toma et al. |
| 2002/0127716 | A1 | 9/2002 | Feron et al. |
| 2002/0169102 | A1 | 11/2002 | Frey, II |
| 2003/0003574 | A1 | 1/2003 | Toma et al. |
| 2004/0033597 | A1 | 2/2004 | Toma et al. |
| 2004/0185429 | A1 | 9/2004 | Kelleher-Andersson et al. |

FOREIGN PATENT DOCUMENTS

| | | |
|---|---|---|
| EP | 0 402 226 A1 | 12/1990 |
| WO | WO 91/09936 | 7/1991 |
| WO | WO 01/30982 | 5/2001 |
| WO | 01/53461 | 7/2001 |
| WO | WO 01/53461 | 7/2001 |
| WO | WO 02/082074 | 10/2002 |
| WO | 03/010243 A2 | 2/2003 |
| WO | 03/010243 A3 | 2/2003 |
| WO | WO 03/063585 | 8/2003 |
| WO | WO 03/064601 | 8/2003 |
| WO | WO 03/089631 | 10/2003 |
| WO | WO 2004/053071 | 6/2004 |
| WO | WO 2006/026222 | 3/2006 |
| WO | WO 2008/027848 | 3/2008 |

OTHER PUBLICATIONS

Archer, D.R., P.A. Cuddon, D. Libsitz, I.D. Duncan. 1997. Myelination of canine central nervous system by glial cell transplantation: A model for repair of human myelin disease. *Nat. Med.* 3:54-59.

Avellana-Adalid, V., B. Nait-Oumesmar, F. Lachapelle, A. Baron-Van Evercooren. 1996. Expansion of rat oligodendrocyte progenitors into proliferative "oligospheres" that retain differentiation potential. *J. Neurosci. Res.* 45:558-570.

Barany, F. 1991. Genetic disease detection and DNA amplification using cloned thermostable ligase. *Proc Natl Acad Sci U S A.* 88:189-93.

Calof, A. L. and D.M. Chikaraishi. 1989. Analysis of neurogenesis in a mammalian neuroepithelium: Proliferation and differentiation of an olfactory neuron precursor in vitro. *Neuron.* 3:115-127.

Calof, A.L., J.S. Mumm, P.C. Rim, J. Shou. 1998. The neuronal stem cell of the olfactory epithelium. *J. Neurobiol.* 36(2):190-205.

Carell, T., E.A. Wintner, A. Bashir-Hashemi, and J. Rebek Jr. 1994a. A novel procedure for the synthesis of libraries containing small organic molecules. *Angewandte Chemie International Edition.* 33(20):2059-2061.

Carell, T., E.A. Wintner, and J. Rebek Jr. 1994b. A solution-phase screening procedure for the isolation of active compounds from a library of molecules. *Angewandte Chemie International Edition.* 33(20):2061-2064.

Case, M. E., M. Schweizer, S.R. Kushner, and N. H. Giles. 1979. Efficient transformation of Neurospora crassa by utilizing hybrid plasmid DNA. *Proc Natl Acad Sci U S A.* 76(10):5259-63.

Cho, C.Y., E.J. Moran, S.R. Cherry, J.C. Stephans, et al. 1993. An unnatural biopolymer. *Science.* 261(5126):1303-5.

Cotton, R. G.H. 1993. Current methods of mutation detection. *Mutat Res.* 285:125-44.

Cronin, M. T., R.V. Fucini, S.M. Kim, R.S. Masino, et al. 1996. Cystic fibrosis mutation detection by hybridization to light-generated DNA probe arrays. *Hum Mutat.* 7:244-55.

Cull, M. G., J.F. Miller, and P.J. Schatz. 1992. Screening for receptor ligands using large libraries of peptides linked to the C terminus of the lac repressor. *Proc Natl Acad Sci U S A.* 89:1865-9.

Cwirla, S. E., E.A. Peters, R.W. Barrett, and W.J. Dower. 1990. Peptides on phage: a vast library of peptides for identifying ligands. *Proc Natl Acad Sci USA.* 87:6378-82.

de Louvencourt, L., H. Fukuhara, H. Heslot, and M. Wesolowski. 1983. Transformation of Kluyveromyces lactis by killer plasmid DNA. *J Bacteriol.* 154(2):737-42.

Devlin, J.J., L.C. Panganiban, and P.E. Devlin. 1990. Random peptide libraries: a source of specific protein binding molecules. *Science.* 249:404-6.

DeWitt, S.H., J.S. Kiely, C.J. Stankovic, M.C. Schroeder, et al. 1993. "Diversomers": an approach to nonpeptide, nonoligomeric chemical diversity. *Proc Natl Acad Sci U S A.* 90:6909-13.

Doucette, R. 1995. Olfactory ensheathing cells: Potential for glial cell transplantation into areas of CNS injury. Histol. and Histopathol. 10:503-507.

Felici, F., L. Castagnoli, A. Musacchio, R. Jappelli, et al. 1991. Selection of antibody ligands from a large library of oligopeptides expressed on a multivalent exposition vector. *J Mol Biol.* 222:301-10.

Feron, F., A. Mackay-Sim, J.L. Andrieu, K.I. Matthaei, A. Holley, and G. Sicard. 1999. Stress induces neurogenesis in non-neuronal cell cultures of adult olfactory epithelium. *Neuroscience.* 88(2):571-583.

Fieck, A., D.L. Wyborski, and J.M. Short. 1992. Modifications of the *E.coli* Lac repressor for expression in eukaryotic cells: effects of nuclear signal sequences on protein activity and nuclear accumulation. *Nucleic Acids Res.* 20(7):1785-91.

Fleer, R., P. Yeh, N. Amellal, I. Maury, et al. 1991. Stable multicopy vectors for high-level secretion of recombinant human serum albumin by Kluyveromyces yeasts. *Biotechnology (NY).* 9:968-75.

Fodor, S.P.A., R.P. Rava, X.C. Huang, A.C. Pease, et al. 1993. Multiplexed biochemical assays with biological chips. *Nature* 364:555-6.

Gallop, M.A., R.W. Barrett, W.J. Dower, S.P. Fodor, et al. 1994. Applications of combinatorial technologies to drug discovery. 1. Background and peptide combinatorial libraries. *J Med Chem.* 37(9):1233-51.

Gasparini, P., A. Bonizzato, M. Dognini, and P.F. Pignatti. 1992. Restriction site generating-polymerase chain reaction (RG-PCR) for the probeless detection of hidden genetic variation: application to the study of some common cystic fibrosis mutations. *Mol Cell Probes.* 6:1-7.

Gibbs, R.A., P.N. Nguyen, and C.T. Caskey. 1989. Detection of single DNA base differences by competitive oligonucleotide priming. *Nucleic Acids Res.* 17(7):2437-49.

Graziadei, P.P.C., M.S. Karlan, G.A. Monti Graziadet, and J.J. Bermstein, 1980. Neurogenesis of Sensory Neurons in the Primate Olfactory System after Section of the Fila Olfactoria. *Brain Research*, 186:289-300.

Gritti, A., E.A. Parati, L. Cova, P. Frolichsthal, et al., 1996. Multipotential stem cells from the adult mouse brain proliferate and self-renew in response to basic fibroblast growth factor. *J. Neurosci.* 16(3):1091-1100.

Grompe, M., D.M. Muzny, and C.T. Caskey. 1989. Scanning detection of mutations in human ornithine transcarbamoylase by chemical mismatch cleavage. *Proc Natl Acad Sci USA.* 86:5888-92.

Hayashi, K., 1992. PCR-SSCP: A method for detection of mutations. *Genetic and Analytical Techniques Applications.* 9(3):73-79.

Houghten, R.A., J.R. Appel, S.E. Blondelle, J.H. Cuervo, et al. 1992. The use of synthetic peptide combinatorial libraries for the identification of bioactive peptides. *Biotechniques*. 13(3):412-21.

Hsu, I.C., Q.P. Yang, M.W. Kahng, and J.F. Xu. 1994. Detection of DNA point mutations with DNA mismatch repair enzymes. *Carcinogenesis*. 15(8):1657-62.

Kalyani, A.J., D. Piper, T. Mujatba, M.T. Lucero, and M.S. Rao. 1998. Spinal cord neuronal precursors generate multiple neuronal phenotypes in culture. *J. Neurosci.* 18(19):7856-7868.

Keen, J., D. Lester, C. Inglehearn, A. Curtis, et al. 1991. Rapid detection of single base mismatches as heteroduplexes on Hydrolink gels. *Trends Genet*. 7:5.

Kelly, J.M. and M.J. Hynes. 1985. Transformation of Aspergillus niger by the amdS gene of Aspergillus nidulans. *Embo J*. 4(2):475-9.

Kozal, M. J., N. Shah, N. Shen, R. Yang, et al. 1996. Extensive polymorphisms observed in HIV-1 clade B protease gene using high-density oligonucleotide arrays. *Nat Med*. 2(7):753-9.

Kukekov, V.G., E.D. Laywell, O. Suslov, K. Davies, et al., 1999. Multipotent stem/progenitor cells with similar properties arise from two neurogenic regions of adult human brain. *Exp. Neurol*. 156:333-344.

Lam, K.S., S.E. Salmon, E.M. Hersh, V.J. Hruby, et al. 1991. A new type of synthetic peptide library for identifying ligand-binding activity, *Nature*. 354:82-84.

Laywell, E.D., V.G. Kukekov, and D.A. Steindler. 1999. Multipotent neurospheres can be derived from forebrain subependymal zone and spinal cord of adult mice after protracted postmortem intervals. *Exp. Neurol*. 156:430-433.

Li, Y., P.M. Field, and G. Raisman. 1997. Repair of adult rat corticospinal tract by transplants of olfactory ensheathing cells. *Science*. 277:2000-2002.

N. Liu, C.B. Shields, and F.J. Roisen. 1998. Primary culture of adult mouse olfactory receptor neurons, *Exp. Neurol*. 151(2):173-183.

MacDonald, K.P.A., W.G. Murrell, P.F. Bartlett, G.R. Bushell, and A. Mackay-Sim. 1996. FGF2 promotes neuronal differentiation in explant cultures of adult and embryonic mouse olfactory epithelium. *J. Neurosci. Res.* 44:27-39.

Mahanthappa, N. K., and G.A. Schwarting. 1993. Peptide growth factor control of olfactory neurogenesis and neuron survival in vitro: Roles of EGF and TGF-β. *Neuron*. 10:293-305.

McEntire, J.K. and S.K. Pixley. 2000. Olfactory receptor neurons in partially purified epithelial cell cultures: Comparison of techniques for partial purification and identification of insulin as an important survival factor, *Chem. Senses*. 25:93-101.

McKay, R. 1997. Stem cells in the central nervous system. *Science*. 276(5309):66-71.

Milward, E.A., S-C. Zhang, M. Zhao, C. Lundberg, et al. 2000. Enhanced proliferation and directd migration of oligodendroglial progenitors co-grafted with growth factor-secreting cells, *GLIA*, 32:264-270.

Mujtaba, T., M. Mayer-Proschel, M.S. Rao. 1998. A common neural progenitor for the CNS and PNS. *Dev. Biol.* 200:1-15.

Murrell, W., G.R. Bushell, J. Livesey, J. McGrath, et al., 1996. Neurogenesis in adult human. *NeuroReport*. 7:1189-1194.

Myers, R.M., Z. Larin, and T. Maniatis. 1985. Detection of single base substitutions by ribonuclease cleavage at mismatches in RNA:DNA duplexes. *Science*. 230:1242-6.

National Inst. of Health, "Stem Cells: A Primer", May, 2000.

Njenga, M.K. and M. Rodriguez. 1996. Animal models of demyelination. *Curr. Opin. Neurol.* 9:159-164.

Orita, M., H. Iwahana, H. Kanazawa, K. Hayashi, et al. 1989. Detection of polymorphisms of human DNA by gel electrophoresis as single-strand conformation polymorphisms. *Proc Natl Acad Sci USA*. 86:2766-70.

Patton, C., L.M. Hatcher, C.L. Lu, K.M. Klueber, and F.J. Roisen, 2001, Abstract Only, "Adult Human Olfactory-Derived Stem Cells: The Effect of Substrata on Proliferation and Lineage Restriction", FASEB Abstracts #797.9.

Powell, A., L.M. Hatcher, C.L. Lu, K.M. Klueber, and F.J. Roisen, 2001 Abstract Only, "Human Olfactory-Derived Stem Cells: The Effect of Time in Culture on Proliferation and Differentiation", FASEB Abstracts #797.10.

Pixley, S.K.,1992. CNS glial cells support in vitro survival, division, and differentiation of dissociated olfactory neuronal progenitor cells. *Neuron*. 8:1191-1204.

Pixley, S.K.., 1992. Purified cultures of keratin-positive olfactory epithelial cells: Identification of a subset as neuronal supporting (sustentacular) cells. *J. Neurosci. Res.* 31:693-707.

Pixley, S.K., M. Bage, D. Miller, M.L. Miller, et al., 1994. Olfactory neurons in vitro show phenotypic orientation in epithelial spheres, *NeuroReport*. 5:543-548.

Prosser, J. 1993. Detecting single-base mutations. *Trends Biotechnol*. 11:238-46.

Rafalko, M., "Amyotrophic Lateral Sclerosis", Indiana State University, undated.

Ramon-Cueto, A., G.W. Plant, J. Avila, and M.B. Bunge. 1998. Long-distance axonal regeneration in the transected adult rat spinal cord is promoted by olfactory ensheathing glia transplants. *J. Neurosci.* 18(10):3808-3815.

Rao, M.S., M. Noble, and M. Mayer-Proschel. 1998. A tripotential glial precursor cell is present in the developing spinal cord. *Proc. Natl. Acad. Sci. USA*. 95:3996-4001.

Reynolds, B.A. and S. Weiss, 1992. Generation of Neurons and Astrocytes from Isolated Cells of the Adult Mammalian Central Nervous System, *Science,* 255:1707-1710.

Roisen, F.J., K.M. Klueber, C.L. Lu, L.M. Hatcher, et al., 2000. Adult human olfactory stem cells, *Brain Research*, 16990:1-12.

Rossiter, B.J.F., and C.T. Caskey. 1990. Molecular scanning methods of mutation detection. *J Biol Chem*. 265(22):12753-6.

Saiki, R.K., T.L. Bugawan, G.T. Horn, K.B. Mullis, et al. 1986. Analysis of enzymatically amplified β-globin and HLA-DQ α DNA with allele-specific oligonucleotide probes. *Nature*. 324:163-6.

Saiki, R.K., P.S. Walsh, C.H. Levenson, and H.A. Erlich. 1989 Genetic analysis of amplified DNA with immobilized sequence-specific oligonucleotide probes, *Proc Natl Acad Sci USA*. 86:6230-4.

Saleeba, J. A. and R.G. Cotton. 1993. Chemical cleavage of mismatch to detect mutations. *Methods Enzymol*. 217:286-95.

Satoh, M. and M. Takeuchi. 1995. Induction of NCAM expression in mouse olfactory keratin-positive basal cells in vitro, *Brain Res.* 87:111-119.

Schade, R., C. Staak, C. Hendriksen, M. Erhard, et. al. 1996. The production of avian (egg yolk) antibodies IgY. The report and recommendations of ECVAM workshop. *Alternatives to Laboratory Animals (ATLA)*, 24:925-934.

Scheffler, B., M. Horn, I. Blumcke, E. Laywell, et al., 1999. Marrow-mindedness: a perspective on neuropoiesis, *TNS*, 22(8):348-357.

Schwob, J.E., S.L. Youngentob and R.C. Mezza, 1995. Reconstitution of the Rat Olfactory Epithelium After Methyl Bromide-Induced Lesion, *J. Comp. Neurol.,* 350:15-37.

Scott, J.K. and G.P. Smith, 1990. Searching for peptide ligands with an epitope library. *Science.* 249:386-90.

Sedky, K., L.M. Hatcher, C.L. Lu, K.M. Klueber, and F.J. Roisen, 2001, Abstract Only, "Adult Murine Olfactory Neuroepithelium: A Source of Neural-Stem Cells", FASEB Abstracts #797.11.

Shihabuddin, L.S., J. Ray, and F.H. Gage, 1997. FGF-2 is sufficient to isolate progenitors found in the adult mammalian spinal cord, *Experim. Neurol.* 148:577-586.

Sosnowski, J.S., M. Gupta, K.H. Reid, and F.J. Roisen, 1995. Chemical traumatization of adult mouse olfactory epithelium in situ stimulates growth and differentiation of olfactory neurons in vitro, *Brain Res.* 702:37-48.

Sreekrishna, K., R.H.B. Potenz, J.A. Cruze, W.R. McCombie, et al.,1988. High level expression of heterologous proteins in methylotrophic yeast Pichia pastoris, *J Basic Microbiol.* 28:265-78.

Tennent, R. and M.I. Chuah, 1996. Ultrastructural study of ensheathing cells in early development of olfactory axons, *Dev. Brain Res.* 95:135-139.

Tilburn, J., C. Scazzocchio, G.G. Taylor, J.H. Zabicky-Zissman, et al., 1983. Transformation by integration in Aspergillus nidulans, *Gene*. 26:205-21.

Vescovi, A.L., E. A. Parati, A. Gritti, P. Poulin, et al., 1999. Isolation and cloning of multipotential stem cells from the embryonic human CNS and establishment of transplantable human neural stem cell lines by epigenet stimulation, *Experim. Neurol.* 156:71-82.

Washington University School of Medicine News Release of Jun. 10, 2000 entitled Scientists Obtain Cells that Repair the Spinal Cord.

Wolozin, B., P. Lesch, R. Lebovits, and T. Sunderland, 1993. Olfactory neuroblasts from Alzheimer donors: studies on APP processing and cell regulation, *Biol. Psychiatry*, 34:824-837.

Wolozin, B., T. Sunderlan, B. Zheng, J. Resau, et al., . Continuous culture of neuronal cells from adult human olfactory epithelium, *J. Mol. Neurosci.* 3:137-146.

Wyborski, D.L., L.C. DuCoeur, and J.M. Short, 1996. Parameters affecting the use of the lac repressor system in eukaryotic cells and transgenic animals. *Environ. Molec. Mutagenesis*, 28:447-58.

Wyborski, D.L. and J.M. Short, 1991. Analysis of inducers of the *E. coli* lac repressor system in mammalian cells and whole animals, *Nucleic Acids Res.* 19(17):4647-53.

Yelton, M.M., J.E. Hamer, and W.E. Timberlake, 1984. Transformation of Aspergillus nidulans by using a trpC plasmid, *Proc. Natl Acad. Sci. USA*, 81:1470-4.

Zhang, S-C, C. Lundberg, D. Lipsitz, L.T. O'Connor, I.D. Duncan. 1998a. Generation of oligodendroglial progenitors from neural stem cells, *J. Neurocytol.* 27:475-489.

Zuckermann, R.N., E.J. Martin, D.C. Spellmeyer, G.B. Stauber, et al. 1994. Discovery of nanomolar ligands for 7-transmembrane G-protein-coupled receptors from a diverse N-(substituted) glycine peptoid library, *J. Med Chem.* 37:2678-85.

Zhang, X., Dissertation "Induction of lineage and differentiation of adult human neuroepithelial progenitors in vitro"., Department of Anatomical Sciences and Neurobiology, University of Louisville, Louisville, Kentucky, (2005).

Nash, H.H., et al., "New method of purification for establishing primary cultures of ensheathing cells from the adult olfactory bulb"., Glia, vol. 34, issue 2, pp. 81-87, (2001).

Vannelli, G.B., et al., "Neuroblast long-term cell cultures from human fetal olfactory epithelium respond to odors"., The Journal of Neuroscience, vol. 15, No. 6, pp. 4382-4394, (1995).

Tissue Culture Laboratory (BIOE342)—Protocol, "Cell Passage", http://www.ruf.rice.edu/~bioewhit/labs/bioe342/docs/cell%20passage.htm, 3 pages, Jul. 28, 2004.

Kalyani, A. et al., "Neuroepithelial stem cells from the embryonic spinal cord: isolation, characterization, and clonal analysis", Developmental Biology, vol. 186, No. 2, pp. 202-223, (1997).

Kukekov, V.G. et al., "A nestin-negative precursor cell from the adult mouse brain gives rise to neurons and glia", GLIA, vol. 21, No. 4, pp. 399-407, (1997).

Marshall, C.T. et al., "Human adult olfactory neuroepithelial derived progenitors retain telomerase activity and lack apoptotic activity", Brain Research, vol. 1045, pp. 45-56, (2005).

Othman, M. et al., "Clonal analysis of adult human olfactory neurosphere forming cells", Biotechnic & Histochemistry, vol. 80, No. 5-6, pp. 189-200, (2005).

Othman, M. et al., "Immunomagnetic separation of adult human olfactory neural progenitors", Biotechnic & Histochemistry, vol. 80, No. 5-6, pp. 177-188, (2005).

Patent database search results for: TTL/"retinoic acid" in the US patent collection, 103 patents, 7 pages, downloaded on Aug. 7, 2006.

Shilo, B.Z. et al., "DNA sequences homologous to vertebrate oncogenes are conserved in Drosophila melanogaster", Proc. Natl. Acad. Science USA, vol. 78, No. 11, pp. 6789-6792, (1981).

Wells, J.A. et al., "Cassette mutagenesis: an efficient method for generation of multiple mutations at defined sites", Gene, vol. 34, pp. 315-323, (1985).

Winstead, W. et al., "Endoscopic biopsy of human olfactory epithelium as a source of viable neural stem cells", American Journal of Rhinology, vol. 19, pp. 83-90, (2005).

Xiao, M. et al., "Human adult olfactory neural progenitors rescue axotomized rodent rubrospinal neurons and promote functional recovery", Experimental Neurology, vol. 194, No. 1, pp. 12-30, (2005).

Zhang, X. et al., "Role of transcription factors in motoneuron differentiation of adult human olfactory neuroepithelial-derived progenitors", Stem Cells Express, vol. 24, No. 2, pp. 434-442, (2006) Epub Sep. 1, 2005 doi:10.1634/stemcells.2005-0171.

Zhang, X. et al., "Induction of neuronal differentiation of adult human olfactory neuroepithelial-derived progenitors", Brain Research, pp. 1073-1074, Feb. 16, 2006, pp. 109-119, Epub Feb. 7, 2006, doi:10.1016/j.brainres.2005.12.059.

Zhang, X. et al., "Induction of oligodendrocytes from adult human olfactory epithelial-derived progenitors by transcription factors", Stem Cells, vol. 23, pp. 442-453, (2005).

Invitrogen, "B-27 Serum-Free Supplements", found at https://catalog.invitrogen.com/index.cfm?fuseaction=viewCatalog.viewProdutDetails&productDescription=147&catname=North%20America%20Main, Jan. 25, 2007.

Product Description "B-27 Supplement 50X", GIBCO Invitrogen Corporation, found at: http://www.invitrogen.com/content/sfs/manuals/3889.pdf, Jun. 2001.

Product Description "B-27 Supplement Minus AO 50X", GIBCO Invitrogen Corporation, found at: http://www.invitrogen.com/content/sfs/manuals/3890.pdf, Jun. 2001.

Product Description "B-27 Supplement (50X), without vitamin A", GIBCO Invitrogen Corporation, found at: http://www.invitrogen.com/content/sfs/manuals/3962%20B27%20without%20Vit%20A%20manual%201169.pdf, Oct. 2003.

Hazel, T., et al., "Culture of neuroepithelial Stem Cells", Current Protocols in Neuroscience, unit 3.1, pp. 3.1.1-3.1.6, (1997).

Wu, Y.Y., et al., Isolation of stem and precursor cells from fetal tissue, Methods in Molecular Biology—Clifton then Totowa, vol. 198, pp. 29-40, (2002).

Pagano, S.F. et al., "Isolation and characterization of neural stem cells from the adult human olfactory bulb", Stem Cells, vol. 18, pp. 295-300, (2000).

Wolozin, B. et al., "Continuous culture of neuronal cells from adult human olfactory epithelium", Journal of Molecular Neuroscience, vol. 3, pp. 137-146, (1992).

International Search Report dated Oct. 2, 2007 for PCT application No. PCT/US03/02292.

Ahmed, S. et al., "BDNF enhances the differentiation but not the survival of CNS stern cell-derived neuronal precursors", J. Neuroscience. 15 (8), pp. 5765-5778, (1995).

Allan D.W. et al.,"Together at last: bHLH and LIM-HD regulators cooperate to specify motor neurons", Neuron, vol. 38, pp. pp. 675-680, (2003).

Appel B. et al., "Retinoids run rampant: Multiple roles during spinal cord and motor neuron development", Neuron, vol. 40, pp. 461-464, (2003).

Arber, S. et al., "Requirement for the homeobox gene H*b*9 in the consolidation of motor neuron identity", Neuron, vol. 23, pp. 659-674, (1999).

Barnett, S.C. et al., "Identification of a human olfactory ensheathing cell that can effect transplant-mediated remyelination of demyelinated CNS axons", Brain, vol. 123, pp. 1581-1588, (2000).

Bibel, M. et al., "Differentiation of mouse embryonic stem cells into a defined neuronal lineage", Nature Neuroscience, vol. 7, No. 9, pp. 1003-1009, (2004).

Bréjot, T. et al., "Forced expression of the motor neuron determinant HB9 in neural stem cells affects neurogenesis", Experimental Neurology, vol. 198, pp. 167-182, (2006).

Briscoe, J. et al., "A homeodomain protein code specifies progenitor cell identity and neuronal fate in the ventral neural tube", Cell, vol. 101, pp. 435-445, (2000).

Britsch S, et al., "The transcription factor SoxI0 is a key regulator of peripheral glial development", Genes Development, vol. 15, pp. 66-78, (2001).

Buytaert-Hoefen, K.A. et al., "Generation of tyrosine hydroxylase positive neurons from human embryonic stem cells after coculture with cellular substrates and exposure to GDNF", Stem Cells, vol. 22, pp. 669-674, (2004).

Calof, A.L. et al., "Analysis of neurogenesis in a mammalian neuroepithelium: Proliferation and differentiation of an olfactory neuron precursor in vitro", Neuron, vol. 3, pp. 115-127, (1989).

Canon, E. et al., "Rapid effects of retinoic acid on CREB and ERK phosphorylation in neuronal cells", Molecular Biokigy of the Cell, vol. 15, pp. 5583-5592, (2004).

Chan, J.R. et al., "NGF controls axonal receptivity to myelination by Schwann cells or oligodendrocytes", Neuron, vol. 43, pp. 183-191, (2004).

Chandran, S. et al., "Differential generation of oligodendrocytes from human and rodent embryonic spinal cord neural precursors", GLIA, vol. 47, pp. 314-324, (2004).
Chiang, M.Y. et al., "An essential role for retinoid receptors RARβ and RXRγ in long-term potentiation and depression", Neuron, vol. 21, pp. 1353-1361, (1998).
Christian, C.N. et al., "Synapse formation between two clonal cell lines", Science, vol. 196, pp. 995-998, (1977).
Corcoran, J. et al., "Nerve growth factor acts via retinoic acid synthesis to stimulate neurite outgrowth". Nature Neuroscience, vol. 2, pp. 307-308, (1999).
Devon, R. et al., "Olfactory ensheathing cells do not require L-ascorbic acid in vitro to assemble a basal lamina or to myelinate dorsal root ganglion neurites", Brain Research, vol. 688, pp. 223-229, (1995).
Duncan, I.D. et al., "Repair of myelin disease: strategies and progress in animal models", Molecular Medicine Today, pp. 554-561, (1997).
Ericson, J. et al., "Pax6 controls progenitor cell identity and neuronal fate in response to graded Shh signaling", Cell, vol. 90, pp. 169-180, (1997).
Farah, M.H. et al., "Generation of neurons by transient expression of neural bHLH proteins in mammalian cells", Development, vol. 127, pp. 693-702, (2000).
Finley, M.F.A. et al., "Synapse formation and establishment of neuronal polarity by P19 embryonic carcinoma cells and embryonic stem cells", J. Neuroscience, vol. 16, pp. 1056-1065, (1996).
Fode, C. et al., "The bHLH protein Neurogenin 2 is a determination factor for epibranchial placode-derived sensory neurons", Neuron, vol. 20, pp. 483-494, (1998).
Fu, H. et al., "Migration and differentiation of *Nkx*-2.2+ oligodendrocyte progenitors in embryonic chicken retina", Developmental Brain Research, vol. 129, pp. 115-118, (2001).
Fu, M. et al., "Sonic hedgehog regulates the proliferation, differentiation, and migration of enteric neural crest cells in gut", J. Cell Biology, vol. 166, pp. 673-684, (2004).
Fu, H. et al., "Dual origin of spinal oligodendrocyte progenitors and evidence for the cooperative role of *Olig2* and *Nkx2.2* in the control of oligodendrocyte differentiation", Development, vol. 129, pp. 681-693, (2002).
Gage, F.H., "Mammalian neural stem cells", Science, vol. 287, pp. 1433-1438, (2000).
Gage, F.H. et al., "Survival and differentiation of adult neuronal progenitor cells transplanted to the adult brain", Proceedings of the National Academy of Science, USA, vol. 92, pp. 11879-11883, (1995).
Gallo, V. et al., "Developmental and growth factor-induced regulation of nest in oligodendrocyte lineage cells", J. Neuroscience, vol. 15, pp. 394-406, (1995).
Graziadei, P.P. et al., "Neurogenesis and neuron regeneration in the olfactory system of mammals, I: Morphological aspects of differentiation and structural organization of the olfactory sensory neurons", J. Neurocytol, vol. 8, pp. 1-18, (1979).
Halilagic, A. et al., "A novel role for retinoids in patterning the avian forebrain during presomite stages", Development, vol. 130, pp. 2039-2050, (2003).
Hanson Jr., M.G. et al., "Cyclic AMP elevation is sufficient to promote the survival of spinal motor neurons in vitro" J. Neuroscience, vol. 18, pp. 7361-7371, (1998).
Hsieh, J., et al., "Histone deacetylase inhibition-mediated neuronal differentiation of multipotent adult neural progenitor cells", Proceedings of the National Academy of Science, USA, vol. 101, pp. 16659-16664, (2004).
Kamachi, Y. et al., "Pairing SOX off: with partners in the regulation of embryonic development", TIG., vol. 16, No. 4, pp. 182-187, (2000).
Kasai, K. et al., "The G12 family of heterotrimeric G proteins and Rho GTPase mediate Sonic hedgehog signalling", Genes to Cells, vol. 9, pp. 49-58, (2004).
Kleitman, N. et al., "Tissue culture methods for the study of myelination", In: Banker G. Goslin K. eds., Culturing Nerve Cells, Cambridge, MA, MIT Press, pp. 337-377, (1991).
Kondo, T. et al., "Sonic hedgehog and retinoic acid synergistically promote sensory fate specification from bone marrow-derived pluripotent stem cells", Proceedings of the National Academy of Science, vol. 102, No. 13, pp. 4789-4794, (2005).
Kuhlbrodt, K. et al., "Sox 10. a novel transcriptional modulator in glial cells", Journal of Neuroscience, vol. 18, pp. 237-250, (1998).
Diez del Corral, R. et al., "Opposing FGF and retinoid pathways control ventral neural pattern, neuronal differentiation, and segmentation during body axis extension", Neuron, vol. 40, pp. 65-79, (2003).
Lee, S.K. et al., "Synchronization of neurogenesis and motor neuron specification by direct coupling of bHLH and homeodomain transcription factors", Neuron, vol. 38, pp. 731-745, (2003).
Leemhuis, J. et al., "Rho GTPases and phosphoinositide 3-kinase organize formation of branched dendrites", Journal of Biological Chemistry, vol. 279, No. 1, pp. 585-596, (2004).
Li, X-J. et al., "Specification of motoneurons from human embryonic stem cells", Nature Biotechnology, vol. 23, No. 2, pp. 215-221, (2005).
Liu, S. et al., "Embryonic stem cells differentiate into oligodendrocytes and myelinate in culture and after spinal cord transplantation", Proceeding of the National Academy of Science, USA, vol. 97, No. 11, pp. 6126-6131, (2000).
Lu, Q.R. et al. "Common developmental requirement for *Olig* function indicates a motor neuron/ oligodendrocyte connection", Cell, vol. 109, pp. 75-86, (2002).
Lu, Q.R. et al., "Sonic hedgehog- regulated oligodendrocyte lineage genes encoding bHLH proteins in the mammalian central nervous system", Neuron, vol. 25, pp. 317-329, (2000).
Ludwin, S.K., "The pathobiology of the oligodendrocyte", Journal of Neuropathology Experimental Neurology, vol. 56, No. 2, pp. 111-124, (1997).
Ma, Q. et al., "Identification of *neurogenin*. a vertebrate neuronal determination gene", Cell, vol. 87, pp. 43-52, (1996).
Maden, M. "Retinoid signalling in the development of the central nervous system", Nature Reviews/Neuroscience, vol. 3, pp. 843-853, (2002).
Marklund, M. et al., "Retinoic acid signalling specifies intermediate character in the developing telencephalon", Development, vol. 131, pp. 4323-4332, (2004).
Marquardt, T. et al., "Cracking the transcriptional code for cell specification in the neural tube", Cell, vol. 106, pp. 651-654, (2001).
Marshall, C.T. et al., "Human adult olfactory neuroepithelial derived progenitors retain telomerase activity and lack apoptotic activity", Brain Research, vol. 1045, pp. 45-56, (2005).
Marshall, C.T., "Characterization of human adult olfactory epithelium-derived stem cells", Dissertation, University of Louisville, School of Medicine, Louisville, Kentucky, (2006).
McKay, R., "Stem cells in the central nervous system", Science, vol. 276, pp. 66-71, (1997).
Meyer-Franke, A. et al., "Depolarization and cAMP elevation rapidly recruit TrkB to the plasma membrane of CNS neurons", Neuron, vol. 21, pp. 681-693, (1998).
Misner, D.L. et al., "Vitamin A deprivation results in reversible loss of hippocampal long-term synaptic plasticity", Proceedings of the National Academy of Science, U S A., vol. 98, pp. 11714-11719, (2001).
Mizuguchi, R. et al., "Combinatorial roles of olig2 and neurogenin2 in the coordinated induction of pan-neuronal neuronal and subtype-specific properties of motoneurons", Neuron, vol. 31, pp. 757-771, (2001).
Moulton, D.G., "Dynamics of cell populations in the olfactory epithelium", Ann. N.Y. Academy Science, vol. 237, pp. 52-61, (1974).
Nelson, P.G. "Central nervous system synapses in cell culture", Cold Sprang Harb Symp Quant Biology, vol. 40, pp. 359-371, (1976).
Nirenberg, M. et al., "Synapse formation by neuroblastoma hybrid cells", Cold Spring Harb Symp Quant Biology, vol. 48, pp. 707-715, (1983).
Noll, E. et al., "Oligodendrocyte precursors originate at the ventral ventricular zone dorsal to the ventral mid-line region in the embryonic rat spinal cord", Development, vol. 118, pp. 563-573, (1993).
Novitch, B.G. et al., "Coordinate regulation of motor neuron subtype identity and pan-neuronal properties by the bHLH repressor Olig2", Neuron, vol. 31, pp. 773-789, (2001).

Novitch, B.G. et al., "A requirement for retinoic acid-mediated transcriptional activation in ventral neural patterning and motor neuron specification", Neuron, vol. 40, pp. 81-95, (2003).

Odden, J.P. et al., "Drosophila *HB9* is expressed in a subset of motoneurons and interneurons, where it regulates gene expression and axon pathfinding", J. Neuroscience, vol. 22, pp. 9143-9149, (2002).

Ono, K. et al., "Early development and dispersal of oligodendrocyte precursors in the embryonic chick spinal cord", Development, vol. 121, pp. 1743-1754, (1995).

Orentas, D.M. et al., "Sonic hedgehog signaling is required during the appearance of spinal cord oligodendrocyte precursors", Development, vol. 126, pp. 2419-2429, (1999).

Othman, M., "Studies on adult mouse and human olfactory derived neural progenitors", Dissertation, University of Louisville, Department of Anatomical Sciences and Neurobiology, Louisville, Kentucky, (2005).

Peirano, R.I. et al., "Protein zero gene expression is regulated by the glial transcription factor Sox10", Molecilar and Cellular Biology, vol. 20, pp. 3198-3209, (2000).

Perrier, A.L. et al., "Derivation of midbrain dopamine neurons from human embryonic stem cells", Proceedings of the National Academy of Science, USA, vol. 101, pp. 12543-12548, (2004).

Plant, G.W. et al., "Purified adult ensheathing glia fail to myelinate axons under culture conditions that enable Schwann cells to form myelin", Journal of Neuroscience, vol. 22, pp. 6083-6091, (2002).

Poncet, C. et al., "Induction of oligodendrocyte progenitors in the trunk neural tube by ventralizing signals: effects of notochord and floor plate grafts, and of sonic hedgehog", Mechanisms of Development, vol. 60, pp. 13-32, (1996).

Pringle, N. P. et al., "Determination of neuro-epithelial cell fate: induction of the oligodendrocyte lineage by ventral midline cells and sonic hedgehog", Developmental Biology, vol. 177, pp. 30-42, (1996).

Qi, Y. et al., "Control of oligodendrocyte differentiation by the Nkx2.2 homeodomain transcription factor", Development, vol. 128, pp. 2723-2733, (2001).

Reh, T.A. "Neural stem cells: Form and function", Nature *Neuroscience*, vol. 5, No. 5, pp. 392-394, (2002).

Richardson, W.D. et al., "Oligodendrocyte lineage and the motor neuron connection", GLIA, vol. 29, pp. 136-142, (2000).

Roelink, H. et al., "Floor plate and motor neuron induction by vhh-I, a vertebrate homolog of hedgehog expressed by the notochord", Cell, vol. 76, pp. 761-775, (1994).

Roelink, H. et al., "Floor plate and motor neuron induction by different concentrations of the amino-terminal cleavage product of sonic hedgehog autoproteolysis", Cell, vol. 81, pp. 445-455, (1995).

Roisen, F.J. et al., "Cyclic adenosine mono-phosphate stimulation of axonal elongation", Science, vol. 175, pp. 73-74, (1972).

Roisen, F.J. et al., "Ganglioside stimulation of axonal sprouting in vitro", Science, vol. 214, pp. 577-578, (1981).

Roisen, F.J. et al., "Dibutyryl cyclic adenosine monophosphate stimulation of colcemid-inhibited axonal elongation", Science, vol. 177, pp. 809-811, (1972).

Roisen, F.J. et al., "Adult human olfactory stem cells", Brain Research, vol. 890, pp. 11-22, (2001).

Rowitch, D.H. et al., "Sonic *hedgehog* regulates proliferation and inhibits differentiation of CNS precursor cells", Journal of Neuroscience, vol. 19, pp. 8954-8965, (1999).

Scardigli, R. et al., "Crossregulation between neurogenin2 and pathways specifying neuronal identity in the spinal cord", Neuron, vol. 31, pp. 203-217, (2001).

Scherer, S.S., "Molecular genetics of demyelination: new wrinkles on an old membrane", Neuron, vol. 18, pp. 13-16, (1997).

Schubert, D. et al., "Cholinergic metabolism and synapse formation by a rat nerve cell line", Proceeding of the National Academy of Science USA, vol. 74, pp. 2579-2583, (1977).

Singh, U.S. et al., "Tissue transglutaminase mediates activation of RhoA and MAP kinase pathways during retinoic acid-induced neuronal differentiation of SH-SYSY cells", J. Biol. Chem., vol. 278, pp. 391-399, (2003).

Slutsky, S.G. et al., "Activation of myelin genes during transdifferentiation from melanoma to glial cell phenotype", J of Biological Chemistry, vol. 278, pp. 8960-8968, (2003).

Snyder, E.Y. et al., "Multipotent neural cell lines can engraft and participate in development of mouse cerebellum", Cell, vol. 68, pp. 33-51, (1992).

Sockanathan, S. et al., "Retinoid receptor signaling in postmitotic motor neurons regulates rostrocaudal positional identity and axonal projection pattern", Neuron, vol. 40, pp. 97-111, (2003).

Sockanathan, S. et al., "Motor neuron-derived retinoid signaling specifies the subtype identity of spinal motor neurons", Cell, vol. 94, pp. 503-514, (1998).

Song, H.J. et al., "Neural stem cells front adult hippocampus develop essential properties of functional CNS neurons", Nat. Neuroscience, vol. 5, pp. 438-445, (2002).

Spoerri, P.E. et al., "Inhibition of conditioned media-mediated neuritogenesis of sensory ganglia by monoclonal antibodies to GMI ganglioside", Brain Research, vol. 469, pp. 71-77, (1988).

Spoerri, P.E. et al., "Calcium regulation of neuronal differentiation: the role of calcium in GM1-mediated neuritogenesis", Brain Research Dev. Brain Research, vol. 56, pp. 177-188, (1990).

Stolt, C.C. et al., "The Sox9 transcription factor determines glial fate choice in the developing spinal cord", Genes Development, vol. 17, pp. 1677-1689, (2003).

Stolt, C.C. et al., "Terminal differentiation of myelin-forming oligodendrocytes depends on the transcription factor Sox10", Genes Development, vol. 16, pp. 165-170, (2002).

Sun, T. et al., "Olig bHLH proteins interact with homeodomain proteins to regulate cell fate acquisition in progenitors of the ventral neural tube", Curr, Biology, vol. 11, pp. 1413-1420, (2001).

Svendsen, C.N., et al., "Survival and differentiation of rat and human epidermal growth factor-responsive precursor cells following grafting into the lesioned adult central nervous system", Experimental Neurology, vol. 137, pp. 376-388, (1996).

Takehayashi, H. et al., "The basic helix-loop-helix factor olig2 is essential for the development of motoneuron and oligodendrocyte lineages", Current. Biology, vol. 12, pp. 1157-1163, (2002).

Tanabe, Y. et al., "Specification of motor neuron identity by the *MNR*2 homeodomain protein", Cell, vol. 95, pp. 67-80, (1998).

Thaler, J., et al., "Active suppression of interneuron programs within developing motor neurons revealed by analysis of homeodomain factor *HB9*", Neuron, vol. 23, pp. 675-687, (1999).

Toresson, H. et al., "Retinoids are produced by glia in the lateral ganglionic eminence and regulate striatal neuron differentiation", Development, vol. 126, pp. 1317-1326, (1999).

Trousse, F. et al. "Notochord and floor plate stimulate oligodendrocyte differentiation in cultures of the chick dorsal neural tube", J. Neuroscience Research, vol. 41, pp. 552-560, (1995).

Warf B.C. et al., "Evidence for the ventral origin of oligodendrocyte precursors in the rat spinal cord", J. Neuroscience, vol. 11, pp. 2477-2488, (1991).

Wichterle, H. et al., "Directed differentiation of embryonic stem cells into motor neurons", Cell, vol. 110, pp. 385-397, (2002).

William, C.M. et al., "Regulation of motor neuron subtype identity by repressor activity of Mnx class homeodomain proteins", Development, vol. 130, pp. 1523-1536, (2003).

Winstead, W. et al., "Endoscopic biopsy of human olfactory epithelium as a source of viable neural stem cells", Am J Rhinol., vol. 19, pp. 83-90, (2005).

Xu X. et al., "Selective expression of Nkx-2.2 transcription factor in chicken oligodendrocyte progenitors and implications for the embryonic origin of oligodendrocytes", Molecular and Cellular Neuroscience, vol. 16, pp. 740-753, (2000).

Zhang J. et al., "The meninges is a source of retinoic acid for the late-developing hindbrain", The Journal of Neuroscience, vol. 23, pp. pp. 7610-7620, (2003).

Zhang, X. et al., "Induction of oligodendrocytes from adult human olfactory epithelial-derived progenitors by transcription factors", Stem Cells, vol. 23, pp. 442-453, (2005).

Zhang, X-D. et al., "The effects of bFGF and BDNF on the cells of injured adult mouse olfactory epithelium in vitro", Acta Physiol Sinica, vol. 52, pp. 193-198, (2000).

Zhang, X. et al., "Adult human olfactory neural progenitors cultured in defined medium", Exp Neurol., vol. 186, pp. 112-123, (2004).

Zhang, X. et al., "Role of transcription factors in the motoneuron differentiation of adult human olfactory neuroepithelial-derived progenitors", Stem Cells, vol. 24, pp. 434-442, (2006).

Zhang, X. et al., "Induction of neuronal differentiation of adult human olfactory neuroepithelial-derived progenitors", Brain Research, Issue 1073-1074, pp. 109-119, (2006).

Zhang, X., "Induction of lineage and differentiation of adult human neuroepithelial progenitors in vitro", Dissertation, University of Louisville, Department of Anatomical Sciences and Neurobiology, Louisville, Kentucky, (2005).

Zhou, Q. et al., "The bHLH transcription factor Olig2 promotes oligodendrocyte differentiation in collaboration with Nkx2.2", Neuron, vol. 31, pp. 791-807, (2001).

Zhou, Q. et al., "The bHLH transcription factors OLIG2 and OLiG1 couple neuronal and glial subtype specification", Cell, vol. 109, pp. 61-73, (2002).

Zhou, Q. et al., "Identification of a novel family of oligodendrocyte lineage-specific basic helix-loop-helix transcription factors", Neuron, vol. 25, pp. 331-343, (2000).

International Search Report dated Mar. 5, 2008 for PCT application No. PCT/US2007/076915.

International Search Report dated Oct. 2, 2007 for PCT application No. PCT/US03/02292.

European Search Report dated May 30, 2008 for PCT application No. PCT/US03/02292.

Roisen, F. J. et al., "Human olfactory epithelial cadaver derived stem cells: An in vitro characterization", Neuroscience Abstract 27, Program # 26.3, (2001).

Beites et al "Identification and molecular regulation of neural stem cells in the olfactory epithelium," *Exp Cell Res*, 2005, 306(2):309-316.

Dulac and Zakhary, "Stem Cells of the Olfactory Epithelium," *Handbook of Stem Cells*, 2004, 2:233-244.

Khalyfa et al., "Gene expression profiling for adult human olfactory neuroepithelial-derived progenitors," *Gene Ther Mol Biol*, 2007, 11:203-216.

Kleinman, *Current Protocols in Cell Biology*, 1998, sections 2.3.1-2.3.6.

Liu et al., "Primary culture of Adult Mouse Olfactory Receptor Neurons," *Exp Neurol*, 1998, 151:173-183.

Marshall et al., "The therapeutic potential of human olfactory-derived stem cells," *Histol Histopathol*, 2006, 21:633-843.

Othman et al., "Identification and culture of olfactory neural progenitors from GFP mice," *Biotech Histochem*, 2003, 78(2):57-70.

Rhinocyte ODDA Designation Letter Approval from Department of Health & Human Services, dated Feb. 1, 2008, 2 pages.

Roisen, Fred J., Curriculum Vitae, Nov. 14, 2008, 17 pages.

Xiao et al., "Human adult olfactory neural progenitors promote axotomized rubrospinal tract axonal reinnervation and locomotor recovery," *Neurobiol Dis*, 2007, 26:363-374.

* cited by examiner

METHODS FOR OBTAINING ADULT HUMAN OLFACTORY PROGENITOR CELLS

RELATED APPLICATIONS

This application incorporates by reference U.S. provisional application Ser. No. 60/279,933 filed on Mar. 29, 2001 and U.S. provisional application Ser. No. 60/352,906, filed on Jan. 28, 2002.

FEDERALLY SPONSORED RESEARCH OR DEVELOPMENT

The subject matter of this application may in part have been funded by the National Institutes of Health, grant no. RR15576. The government may have certain rights in this invention.

BACKGROUND OF THE INVENTION

Stem cell transplants have broken new ground in disease research. Many believe that stem cells are the keys capable of unlocking treatments for some of the world's most devastating diseases, including cancer, multiple sclerosis, Alzheimer's disease, spinal cord injuries and Parkinson's disease. However, the benefits and successes of stem cell research are often overshadowed by moral and ethical considerations because the most versatile stem cells used in research and treatments originate from human embryos or aborted fetal tissues. These ethical concerns are often weighed against the ability of stem cells to revolutionize the practice of medicine and improve the quality and length of life. The potential answers and treatments stem cells promise have spurred many research efforts, even in the face of moral and ethical concerns.

Initially, pluripotent stem cells were isolated and developed from two sources: directly from the inner cell mass of human embryos at the blastocyst stage and from fetal tissue obtained from terminated pregnancies. However with the significant advantages to be gained from use of stem cells, researchers have been searching for a source of these cells, in adults, that would allow them to avoid the ethical debate associated with the use of stem cells derived from embryos and fetal tissues. Multipotent stem cells have not been found for all types of adult tissue, but discoveries in this area of research are increasing. For example, until recently, it was thought that stem cells were not present in the adult nervous system, but in recent years, neuronal stem cells have been isolated from the adult rat and mouse nervous systems.

While the possibility of deriving stem cells from adult tissue sources holds real promise, there are also some significant limitations. First, adult stem cells are often present in only minute quantities, are difficult to isolate and purify, and their number may decrease with age. Further, although stem cells have been isolated from diverse regions of the adult central nervous system (CNS), they cannot be removed from any of these locations without serious consequences to the donor (A. Gritti, et. al., 1996; V. G. Kukekov, et al., 1997).

Due to the difficulties associated with deriving stem cells from adult tissues, typically fetal and neonatal olfactory bulbs have been used as a source of cells for transplantation into regions of the nervous system. (See for example, Njenga, M. K and M. Rodriguez, 1998; Rao, M. S., 1999; R. Tennent, and M. I. Chuah, 1996; Li, Y, et. al., 2000). For example, Archer et al., transplanted fetal glial cells into the canine CNS and showed that the transplanted cells caused a large scale remyelination of demyelinated cells and long term survival of these cells. Archer et al compared results achieved by transplanting fetal cells with those achieved by transplanting adult cells and found that the fetal cells were more capable of remyelination and survived longer. (Archer et. al., 1997).

Other researchers have avoided the ethical debate of using embryonic and fetal stem cells by using other cells and tissues, and more specifically by using adult olfactory bulb tissue, isolated from the brain, for spinal cord repair. For example, Li et al. grafted ensheathment cells from the olfactory bulb into a damaged spinal cord and enabled regeneration of corticospinal tract neurons in the region of the graft (Li, Y., et. al., 2000). Ramon-Cueto et. al. have shown that olfactory bulb ensheathment cells, removed from the bulb, help regenerating spinal cord axons cross a gap in the spinal cord (Ramon-Cueto et. al., 1998). Doucette found that ensheathing cells can adopt several different roles as the need arises. Specifically they are able to switch their phenotype from that resembling an astrocyte to that of a myelinating Schwann cell (R. Doucette, 1995).

The unique regenerative capacity of olfactory neuroepithelium (ONe), found in the nasal cavity, has been well documented in numerous reports. The presence of a stem cell population in ONe with the capacity to produce both neurons and their ensheathment and supporting cells is well known (A. L. Calof, et. al., 1998). Still the difficulty has not been in knowing where adult stem cells are but rather in actually locating and isolating adult stem cells, and maintaining them in a mitotically active state. Others have established cultures of viable stem cells from various sources including embryonic mice (A. L. Calof et. al., 1989, 1998), embryonic rats (A. Kalyani, et. al., 1997; T. Mujaba et. al., 1998; M. S. Rao et. al., 1998; and L. S. Shihabuddin et al., 1997) and neonatal mice and rats (N. K. Mahanthappa et. al., 1993; J. K. McEntire et. al., 2000; S. K. Pixley, 1992, 1994; and M. Satoh and M. Takeuchi, 1995). Cultures from adult mice and rats, (A. L. Calof, et. al., 1998, 1989; F. Feron, et. al., 1999; A. Gritti, et. al., 1996; E. D. Laywell, et. al., 1999; N. Liu, et. al., 1998; K. P. A. Mac Donald, et. al., 1996; and J. S. Sosnowski, et. al., 1995) human embryos, (A. L. Vescovi et. al., 1999) biopsies from patients with Alzheimer's disease (B. Wolozin et. al., 1993) and normal human adults (F. Feron, et. al., 1999; W. Murrel, et. al., 1996; and B. Wolozin, et. al., 1992) have produced viable ONe cultures but none have produced stem or neurosphere-forming cells. Instead, each of these cultures contained committed neurons, glia and epithelial cells.

Therefore identifying a source of readily accessible adult autologous neural stem cells that can be obtained without permanent damage to the donor individual would be of great benefit not only because it avoids the ethical concerns associated with using embryonic and fetal stem cells, but also by providing powerful tools for developing treatments, increasing the successes of transplantation techniques, and by providing methods for diagnostic and drug development evaluations.

BRIEF SUMMARY OF THE INVENTION

In a first aspect, the present invention is an isolated human olfactory stem cell.

In a second aspect, the present invention is a cell culture of an isolated human olfactory stem cell.

In a third aspect, the present invention is a method of isolating cells, by culturing human tissue from olfactory neuroepithelium to form neurospheres.

In a fourth aspect, the present invention is a method of forming a cell culture by isolating cells obtained from culturing human tissue from the olfactory neuroepithelium to form neurospheres and then contacting the isolated cells with a differentiation factor.

In a fifth aspect, the present invention is a method of forming a differentiated cell, by contacting an isolated human olfactory stem cell with a differentiation factor.

In a sixth aspect, the present invention is a method of treating a neurological disorder by transplanting a plurality of isolated human olfactory stem cells.

In a seventh aspect, the present invention is a method of treating a neurological disorder by transplanting a plurality of cells differentiated by contacting an isolated human olfactory stem cell with a differentiation factor.

In an eighth aspect, the present invention is a method of treating a neurological disorder by isolating a plurality of cells by culturing human tissue from olfactory neuroepithelium to form neurospheres and transplanting a plurality of these isolated human olfactory stem cells.

In a ninth aspect, the present invention is a method of evaluating a compound for neurological effects by contacting an isolated human stem cell with the compound.

In a tenth aspect, the present invention is a kit with a plurality of human olfactory stem cells.

DETAILED DESCRIPTION OF THE INVENTION

Figure 1:
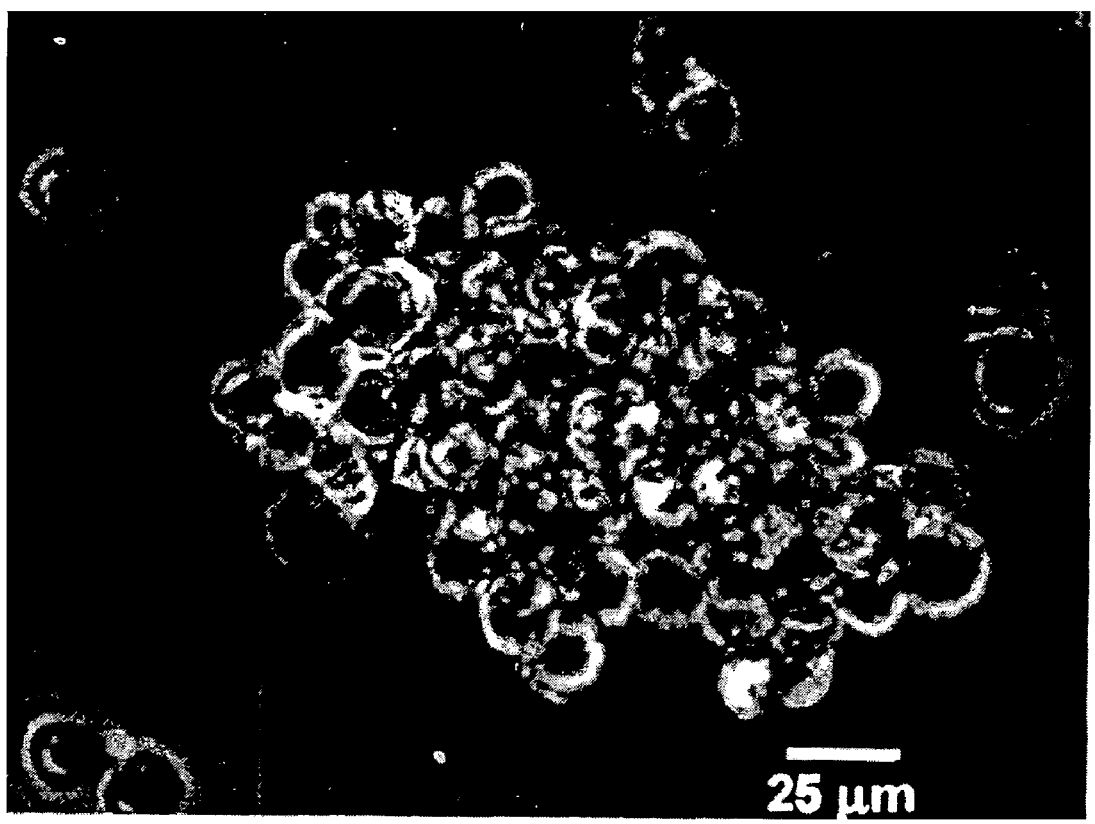
FIG. 1. Human ONe neurospheres.

That human ONe can be manipulated in vitro to form neurospheres from donors as old as 95 years of age, demonstrates a remarkable degree of neuroplasticity in these cells. Furthermore the direct, minimally invasive surgical accessibility of human ONe, coupled with its pluripotency, makes this a good autologous source of stem cells. These cells can be removed, expanded, and manipulated ex vivo prior to return, via transplantation, to the donor for regeneration of damaged neural tissue. These pluripotent stem cells can also be used to generate patient-specific genetic diagnostic evaluation and treatment.

ONe provides a source of viable adult pluripotent stem cells, capable of use in research, treatments, drug development, and transplantations, which avoids the ethical concerns associated with use of embryonic and fetal stem cells. Even further, use of ONe avoids ethical concerns associated with the use of animal models and can even be used where there are no animal models. ONe has a life long regenerative capacity; stem cells located within the ONe replace aging and damaged neurons and their sustentacular cells. The accessibility of ONe and proliferative capacity make it a unique source for progenitor cells. Further the ability to obtain ONe pluripotent stem cells from the nasal cavity eliminates the need to use highly invasive and damaging procedures that are currently available to obtain post-embryonic stem cells. In addition, since one of the greatest problems encountered in transplantations is tissue rejection, providing stem cells for autologous transplantation eliminates the need to wait for a histocompatible donor and thereby greatly reduces both the frequency and severity of rejection. The present invention also can provide a source of stem cells from individuals with unique nervous system disorders such as bi-polar disorder, schizophrenia or amyotrophic lateral sclerosis for use in drug or treatment development. The present invention also has the advantage of generating patient-specific cell populations for immunological, pharmacological and genetic diagnostic evaluations.

II. Definitions

A. Cell Types

A cell that is "totipotent" is one that may differentiate into any type of cell and thus form a new organism or regenerate any part of an organism.

A "pluripotent" cell is one that has an unfixed developmental path, and consequently may differentiate into various differentiated cell types, for example, neurons, oligodendrocytes, astrocytes, ensheathing cells or glial cells. Pluripotent cells resemble totipotent cells in that they are able to develop into other cell types; however, various pluripotent cells may be limited in the number of developmental pathways they may travel.

A "multi potent cell" is a cell that is derived from a pluripotent pre-cursor and can differentiate into fewer cell types than this pluripotent pre-cursor.

A "stem cell" describes any precursor cell, capable of self-renewal, whose daughter cells may differentiate into other cell types. In general, a stem cell is capable of extensive proliferation, generating more stem cells (self-renewal) as well as more differentiated progeny. Thus, a single stem cell can generate millions of differentiated cells as well as other stem cells. Stem cells provide a continuous source of tissue precursor cells.

Stem cells may divide asymmetrically, with one daughter cell retaining the stem state and the other expressing some distinct other specific function and phenotype. Alternatively, some of the stem cells in a population can divide symmetrically into two stems, thus maintaining some stem cells in the population as a whole, while other cells in the population give rise only to differentiated progeny. Researchers have noted that cells that begin as stem cells might proceed toward a differentiated phenotype, such as a neuron, but then "reverse" and re-express the stem cell phenotype upon implantation.

"Human olfactory stem cell" means a cell which is human, as determined by the chromosome structure or reaction with human specific antibodies, and has at least two of the following characteristics, and preferably has at least three of the following characteristics, more preferably has least four of the following characteristics, still more preferably has at least five of the following characteristics and most preferably has all of the following characteristics:

divides every 18-24 hours for over 200 passages;

immunoreactivity for the marker β-tubulin isotype III is significantly elevated when the cell is grown on various substratum, such as a matrix coated with a mixture of enctanin, laminin and collagen IV (ECL-matrix) alternatively laminin or fibronectin may also be used;

immunoreactivity for β-tubulin isotype III is much higher than other cell types immunoreactivity for this marker;

addition of dibutyryl cAMP to the culture growing on ECL-matrix causes the cells to form processes;

immunopositive for NCAM marker; or does not require a feeder layer for growth and proliferation.

The human olfactory stem cell may not have all of the aforementioned characteristics, but will have at least two of these characteristics simultaneously.

Preferably human olfactory stem cells will propagate in culture and can differentiate into one or more of the following cell types: neurons, ensheathing cells, epithelial cells or astrocytes.

A "neurosphere" is a cluster of about 20 to 80 mitotically active neuronal or glial pre-cursor cells. Generally neurospheres represent a population of neural cells in different stages of maturation formed by a single, clonally expanding pre-cursor that forms spherical, tightly packed cellular structures.

An "oligosphere" is a cluster of mitotically active oligodendrocyte, pre-cursor cells. Generally oligospheres represent a population of oligodendrocytes in different stages of maturation formed by a single, clonally expanding pre-cursor that forms spherical, tightly packed cellular structures. (V. Avellana-Adalid, et. al., 1996; S. C. Zhang, et. al., 1998).

"Post-embryonic" cells include any cells present in a vertebrate at any stage after birth.

B. Characterization of Cell Types

"Isolated" means outside of the body or ex vivo and containing at least 10% of the human olfactory stem cell, including cells that may be frozen individually or are frozen in a clump or cluster.

A "marker" is used to determine the differentiated state of a cell. Markers are characteristic, whether morphological or biochemical (enzymatic), particular to a cell type, or molecules expressed by the cell type. Preferably, such markers are proteins, and more preferably possess an epitope for antibodies or other binding molecules available. However, a marker may comprise any molecule found in a cell, including but not limited to, proteins (peptides and polypeptides), lipids, polysaccharides, gangliosides, nucleic acids, steroids and derivatives thereof.

Markers may be detected by any method available to one of skill in the art. In addition to antibodies (and all antibody derivatives) that recognize and bind to at least one epitope on a marker molecule, markers may be detected using analytical techniques, such as by protein dot blots, sodium dodecyl sulfate polyacrylamide gel electrophoresis (SDS-PAGE), or any other gel system that separates proteins, with subsequent visualization of the marker (such as Western blots), gel filtration, affinity column purification; morphologically, such as fluorescent-activated cell sorting (FACS), staining with dyes that have a specific reaction with a marker molecule (such as ruthenium red and extracellular matrix molecules), specific morphological characteristics (such as the presence of microvilli in epithelia, or the pseudopodia/filopodia in migrating cells, such as fibroblasts and mesenchyme); and biochemically, such as assaying for an enzymatic product or intermediate, or the overall composition of a cell, such as the ratio of protein to lipid, or lipid to sugar, or even the ratio of two specific lipids to each other, or polysaccharides. In the case of nucleic acid markers, any known method may be used. If such a marker is a nucleic acid, PCR, RT-PCR, in situ hybridization, dot-blot hybridization, Northern blots, Southern blots and the like may be used, coupled with suitable detection methods.

A marker or a combination of markers will show specificity to a cell type. Myofibrils, for example, are characteristic solely of muscle cells; axons are only found in nervous tissue, cadherins are typical of epithelia, β2-integrins to white blood cells of the immune system, and a high lipid content characteristic of oligodendrocytes while lipid droplets are unique to adipocytes. See Table 1 below for a list of Markers that may be used in the present invention.

TABLE 1

Markers for use in identification of cell types

| Antibodies and Growth Factor Receptors | Useful dilutions when the diluent is the described antibody or growth factor | Target | Source* |
| --- | --- | --- | --- |
| Trk A, B, C or pan | 1:100 | Neurotrophin receptors | Santa Cruz BioTech, Santa Cruz, CA |
| NGF receptor p 75$^{NGFR}$, human monoclonal | 1:50 | Neurons and glia | Sigma, St. Louis, MO |
| GFAP, polyclonal | no dilution | Ensheathment progenitor | INCSTAR, Stillwater, MN |
| GFAP, monoclonal | 1:40 | Ensheathment progenitor, astrocytes, olfactory glia | Boehringer Mannheim, Indianapolis, IN |
| A2B5, monoclonal | 1:100 | Glia, some neurons | Boehringer Mannheim, Indianapolis, IN |
| β-tubulin isotype III | clone | Neurons, progenitor cells | Sigma, St. Louis, MO |
| Monoclonal MAP2ab | 1:250 | Neurons | Boehringer Mannheim, Indianapolis, IN |
| Cytokeratin, CK5/6 | 1:20 | Epithelial | Boehringer Mannheim, Indianapolis, IN |
| E-NCAM (5A5), monoclonal | dilution undetermined | Neurons | DSHB, University of Iowa, IA |
| NCAM, monoclonal | 1:50 | Neurons | Chemicon International, Temecula, CA |
| Alpha-internexin | 1:50 | Immature neurons | Chemicon International, Temecula, CA |
| Nestin, monoclonal | 1:50 | Embryonic stem cells | Chemicon International, Temecula, CA |
| Nestin, polyclonal | 1:40 | neuronal stem cells | (R. McKay, 1997) |
| mAb against actin | 1:100 | Microfilaments | Boehringer Mannheim, Indianapolis, IN |
| pAb against tubulin | 1:20 | Microtubules | ICN Biochemicals, Costa Mesa, CA |
| mAb against tubulin | 1:500 | Microtubules | Amersham, Arlington Heights, IL |
| RIP, polyclonal | 1:20 | Mature oligodendrocytes | Zymed, San Francisco, CA |

*Alternatively if these commercial antibodies are not available, one of skill in the art will know how to make antibodies. For example, an antibody may be made in the following manner.

Polyclonal antibodies can be raised against a mammalian host by one or more injections of an immunogen and, if desired, an adjuvant. Typically, the immunogen (and adjuvant) is injected in the mammal by a subcutaneous or intraperitoneal injection. The immunogen may include molecules such as polypeptides, whole cells or fractions of cells and may be recombinantly produced or non-recombinantly produced. Examples of adjuvants include Freund's complete and monophosphoryl Lipid A synthetic-trehalose dicorynomycolate (MPL-TDM). To improve the immune response, an immunogen may be conjugated to a polypeptide that is immunogenic in the host, such as keyhole limpet hemocyanin (KLH), serum albumin, bovine thyroglobulin, and soybean trypsin inhibitor. Protocols for antibody production are well-known (Harlow and Lane, 1988). Alternatively, pAbs may be made in chickens, producing IgY molecules (Schade et. al., 1996).

Monoclonal antibodies (mAb) may also be made by immunizing a host, or lymphocytes from a host, harvesting the mAb secreting (or potentially secreting) lymphocytes, fusing the lymphocytes to immortalized cells, and selecting those cells that secrete the desired mAb. The mAbs may be isolated or purified from the culture medium or ascites fluid by conventional procedures such as polypeptide A-Sepharose, hydroxylapatite chromatography, gel electrophoresis, dialysis, ammonium sulfate precipitation or affinity chromatography (Harlow and Lane, 1988; Harlow and Lane, 1999.)

"Plasticity" describes the ability of a cell to vary in developmental pattern, i.e. the ability to be molded or altered. Preferably a cell that demonstrates "plasticity" demonstrates the ability to differentiate into various cell types.

"Differentiation" describes the acquisition or possession of one or more characteristics or functions different from that of the predecessor cell type. A differentiated cell is one that has a different character or function from the surrounding structures or from the precursor of that cell (even the same cell). Differentiation gives rise from a limited set of cells (for example, in vertebrates, the three germ layers of the embryo: ectoderm, mesoderm and endoderm) to cellular diversity, creating all of the many specialized cell types that comprise an individual.

Differentiation is a developmental process whereby cells assume a specialized phenotype, i.e. acquire one or more characteristic or functions distinct from other cell types. In most uses, the differentiated phenotype refers to a cell phenotype that is at the mature endpoint in some developmental pathway. In many but not all tissues, the process of differentiation is coupled with exit from the cell cycle; in these cases, the cell loses or is greatly restricted in its capacity to proliferate.

A "differentiation factor" is any chemical or thing that will cause differentiation. This includes, for example, substrates and growth factors.

In general, a "growth factor" is a substance that promotes cell growth and development by directing cell maturation and differentiation. Growth factors may also mediate tissue maintenance and repair. Growth factors are ligated by specific receptors and act at very low concentrations. Many growth factors are mediated, at least partially, by second messengers, such as cyclic AMP (cAMP). Members of the neurotrophin family (NGF, BDNF, NT3 and NT4/5) play a key role in neuronal development, differentiation and survival. Growth factors of the neurotrophin family typically act through tyrosine kinase receptors (Trks).

A "neurological disorder" is any disorder, including psychiatric disorders, affecting a part of the nervous system, such as the nerves, spinal cord, or brain. Some examples of neurological disorders would include Parkinson's disease, Alzheimer's disease, multiple sclerosis, amyotrophic lateral sclerosis, spinal cord injury, schizophrenia, autism and bipolar disorder.

A "neurotransmitter" is any chemical or substance capable of inhibiting or exciting a postsynaptic cell. Some examples of neurotransmitters includes dopamine, serotonin and acetylcholine. It is well known that improper levels of neurotransmitters are associated with numerous disorders, including neurological disorders as described above.

"Neurotigenesis" is the formation of new processes and extension of existing processes resembling those of neurons.

II. Isolating Human Olfactory Stem Cells

ONe tissue is first removed from the nasal cavity. The skilled artisan will appreciate that the ONe tissue may be removed using a variety of methods. A preferred method of removing the ONe tissue involves the use of an endoscope, having a fiber optic cable with a "pincher" at one end, to take a biopsy. An advantage of using this preferred method is the ability to obtain tissue samples from live donor individuals, with minimal invasiveness and discomfort. A further advantage of removing ONe tissues using an endoscope is the ability to freeze or culture the ONe stem cells obtained in an initial collection and the ability to take multiple collections when needed for in vitro culture viability or to reach a desired level of stem cell quantity.

A lateral rhinotomy is another method for removing ONe tissues. A lateral rhinotomy is an operative procedure in which the nose is incised along one side so that it may be turned away to provide full access to the nasal cavity and ONe tissue. However this procedure is highly invasive. In a preferred method, the lateral rhinotomy procedure is utilized to remove ONe tissues from a cadaver. In this method, the cadaver is preferably no more than eighteen hours postmortem and more preferably is six hours postmortem and most preferably, the cadaver is immediately postmortem.

Once removed, the ONe may be cultured. For example, ONe is cultured in medium containing DMEM (Dulbecco's Modified Eagle Medium) and F12 (1:1) with 10% heat-inactivated fetal bovine serum (FBS) (all media components from GIBCO, Grand Island, N.Y.). Other media may be appropriate, as recognized by the skilled artisan, as well as different animal sources of sera or the use of serum-free media; furthermore, some cultures will require additional supplements, including amino acids (such as glutamine), growth factors, etc. A variety of substrata may be used to culture the cells, for example, plastic or glass, coated or uncoated substrata may be used. For example, the culture plate may be a laminin-fibronectin coated plastic plate. Alternatively the substrata may be coated with extracellular matrix molecules (to encourage adhesion or to control cellular differentiation), collagen or poly-L-lysine (to encourage adhesion free of biological effects). The cell culture substrata may also be treated to be charged. In the case where substratum adhesion is undesired, spinner cultures may be used, wherein cells are kept in suspension. Further the composition of the substrata can play a role in differentiation of ONe stem cells.

The removed ONe not only contains pluripotent stem cells, but it may also contain olfactory receptor neurons (ORNs), olfactory ensheathment or sustentacular cells (OECs), epithelial supporting cells, and fibroblasts. After culturing for several weeks, a population of mitotically active cells emerge, while the ORNs and OECs become vacuolated, retract their processes, and die after approximately three weeks in vitro. These mitotically active cells double every day. After 2-3 weeks of additional undisturbed proliferation neurospheres begin to form. However this occurs in only 5-10% of the cultures so multiple cultures are generally needed to form and sustain a collection of cells. The neurosphere cells are collected from the culture. A variety of methods may be used to collect the neurospheres, including enzymatic removal (such as by trypsination), chemical methods, (e.g. cation metal chelation using Ethylenediaminetetraacetic Acid (EDTA) or Ethylene,Glycol-bis(β-aminoethyl Ether) N,N,N',N'-Tetraacetic Acid (EGTA), and mechanically, such as by cell scraping or in the case of suspension cells, by simple centrifugation. After harvest, cells may be washed and separated from unwanted debris by centrifugation with or without a gradient (continuous or step, such as with polyethylene glycol or sucrose), or sorted, if desired by FACS or other binding-based techniques, such as antibodies to a specific cell marker coated on (magnetic) beads. Preferably, all collection methods are performed aseptically. One of skill in the art will know how to properly determine useful parameters, such as incubation times with cell removal agents (chemical or enzymatic), temperatures, centrifugal force, and number and type of washes. After collection, the neurospheres are mechanically dispersed into individual cells, repeatedly washed with an osmotically-appropriate (buffered or unbuffered) solution, usually provided by salt solutions, such as saline's or Ringer's solution and centrifuged to remove cell debris, and then replated at $10^3$ cells per $mm^2$.

The cells may be further isolated from these replated cells and characterized by probing the cells with lineage-specific antibodies, or examined for other useful markers. Initially it is preferred to determine whether neurons are present in the isolated cell cultures. In addition to simple microscopic inspection, neurons may be more sensitively detected by at least the following markers: NCAM, E-NCAM, monoclonal MAP2ab, β-tubulin isotype III, A2B5 and NGF receptor (Table 1). Glial cells may be detected by at least the presence of a glial membrane enriched ganglioside with a monoclonal antibody, such as A2B5. Astrocytes may be detected at least by the presence of glial fibrillary acid protein (GFAP). Table 2 summarizes the immunoreactivity of ONe neurosphere cells which contain human olfactory stem cells.

TABLE 2

Summary of immunoreactivity of subcultured neurosphere cells from ONe

Antigen Expressed
NCAM+/Nestin+−**
NCAM+/Keratin−
β-tubulin III+/Nestin+−**
β-tubulin III+/GFAP−
GFAP+/β-tubulin III−
GFAP+/RIP−
GFAP+/A2B5+
Trk A+/p75$^{NGFR}$ −
Trk B+/p75$^{NGFR}$ −

**+−means that there are both immunopositive and immunonegative cells wherein at least more than one cell is immunonegative but not all cells are immunonegative.

III. Cell Cultures

Suitable medium and conditions for generating primary cultures and maintaining the above neurosphere cultures are well known in the art and can vary depending on the cell types present. For example, skeletal muscle, bone, neurons, skin, liver and embryonic stem cells are all grown in media differing in their specific contents. Furthermore, media for one cell type may differ significantly from lab to lab and institution to institution. To keep cells dividing, serum, such as fetal calf serum, is added to the medium in relatively large quantities, 1-30% by volume, again depending on cell or tissue type. Specific purified growth factors or cocktails of multiple growth factors can also be added or are sometimes substituted for serum. When differentiation is desired and not proliferation, serum with its mitogens is generally limited to about 0-2% by volume. Specific factors or hormones that promote differentiation and/or promote cell cycle arrest can also be used.

Physiologic oxygen and subatmospheric oxygen conditions can be used at any time during the growth and differentiation of cells in culture, as a critical adjunct to selection of specific cell phenotypes, growth and proliferation of specific cell types, or differentiation of specific cell types. In general, physiologic or low oxygen-level culturing is accompanied by methods that limit acidosis of the cultures, such as addition of strong buffer to medium (such as HEPES), and frequent medium changes and changes in $CO_2$ concentration.

In addition to oxygen, the other gases for culture typically are about 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5%, but may vary between 2-10%. Both nitric oxide and carbon monoxide, when necessary, are typically administered in very small amounts (i.e. in the ppm range), determined empirically or from the literature.

The medium can be supplemented with a variety of growth factors, cytokines, serum, etc. Examples of suitable growth factors are basic fibroblast growth factor (bFGF), neuronal growth factor (NGF), NT3, NT4/5, brain-derived neuronal factor (BDNFs) and colony stimulating factor (CSF). Examples of hormone medium additives are estrogen, progesterone, testosterone or glucocorticoids such as dexamethasone. Examples of cytokine medium additives are interferons, interleukins, or tumor necrosis factor-α (TNFα). One skilled in the art will test additives and culture components in different culture conditions, as these may alter cell response, active lifetime of additives or other features affecting their bioactivity. In addition, the surface on which the cells are grown can be plated with a variety of substrates that contribute to survival, growth and/or differentiation of the cells. These substrates include but are not limited to laminin, ECL-matrix, collagen, poly-L-lysine, poly-D-lysine, polyornithine and fibronectin. In some instances, when 3-dimensional cultures are desired, extracellular matrix gels may be used, such as collagen, ECL-matrix, or gelatin. Cells may be grown on top of such matrices, or may be cast within the gels themselves. For example, the use of an ECL-matrix, promoted the lineage restriction of the ONe derived cells toward maturing neurons as indicated by the level of neurotigenesis.

IV. Transplantation

The stem cells of the present invention may be transplanted into a patient suffering from a neurological disorder, such as spinal cord injury, Alzheimer's disease, Parkinson's disease, amyotrophic lateral sclerosis or multiple sclerosis, as a method of treating the disorder. Methods of transplantation include injection of transformed cells effective for treating a neurological disorder, via a variety of methods, at the site of injury or a distant site. The cells may be partial or completely differentiated prior to transplantation.

V. Reformation or Formation of CNS Structures

The stem cells of the invention may further be used to form or reform damaged or malfunctioning CNS structures, such as axons or encourage regrowth of existing axons. For example, Li et. al. have demonstrated that injection of ensheathing cells cultured from adult rat olfactory bulb, at a site of transection of the upper cervical corticospinal tract, induced unbranched, elongative growth of the cut corticospinal axons and restored motor function (Li et. al., 2000). Similarly, the stem cells may be differentiated, and the resulting ensheathing cells selected and transplanted to repair spinal damage.

The differentiation of stem cells can be directed to result in a particular type of daughter cell arising from the parent stem cell. For example when the stem cell of the present invention is exposed to dibutryl cAMP for 24 hours, it differentiates into a progenitor containing a neurofilament precursor. Furthermore, in culture, at least a portion of the stem cells spontaneously differentiate and may be selected. Freezing may be used to store the differentiated cells until enough are collected for an effective transplantation. Therefore by inducing the stem cell of the present invention to form a desired cell type, and injecting this differentiated cell into the site of injury, CNS structures may be treated.

VI. Pharmacological Approaches

The cells of the present invention may be used to manufacture pharmaceutically useful compounds, such as dopamine or other neurotransmitters produced by healthy neurons. Therefore by directing the stem cell of the present invention down a differentiation pathway leading to neuron formation, a unique cell culture comprised of differentiated neurons derived from the stem cell of the present invention can provide large cell populations capable of producing large amounts of pharmaceutically useful compounds, such as dopamine. Further, many growth factors, including at least NGF, BDNF, NT3 and NT4/5 may be used to direct the stem cell to differentiate.

Second messengers, such as cAMP may be used to mediate the interaction between the growth factor receptors of the differentiating stem cell and the growth factors themselves. For example, exposure of neurosphere subcultures to media containing 2.5 mM dibutyryl cAMP drastically decreases mitotic activity and increases in the levels of α-internexin, a neuronal marker that appears prior to neurofilament formation in developing neurons.

Additionally, the cells of the invention may be manipulated to express transgenes that encode useful products. An advantage of engineering the cells of the invention, whether differentiated or not, is the possibility of producing polypeptides, such as neuronal polypeptides or stem-cell specific polypeptides that are processed in a manner that they would be in their native context and can thus be cultured in large quantities. Another advantage includes the engineering of such cells prior to transplantation to a subject such that a therapeutically useful molecule is expressed; for example, a patient suffering from Parkinson's disease can have ONe cells harvested to create the stem cells of the invention, but they will not express sufficient dopamine to treat Parkinson's disease. Thus such cells can be engineered with a wild-type dopamine gene (either operably linked to the endogenous dopamine promoters or to an exogenous promoter, depending on the regulation and quantity of secretion that is desired) before implantation VII. Recombinant DNA Manipulation of Cells To manipulate DNA in vitro so that the cells of the invention are engineered with exogenous nucleic acid sequences, many techniques are available to those skilled in the art (Ausubel et al., 1987).

Vectors are tools used to shuttle DNA between host cells or as a means to express a nucleotide sequence. Some vectors function only in prokaryotes, while others function in both prokaryotes and eukaryotes, enabling large-scale DNA preparation from prokaryotes for expression in eukaryotes. Inserting the DNA of interest is accomplished by ligation techniques and/or mating protocols well known to the skilled artisan. Such DNA is inserted such that its integration does not disrupt any necessary components of the vector. In the case of vectors that are used to express the inserted encoded polypeptide, the introduced DNA is operably-linked to vector elements that govern its transcription and translation. "Operably-linked" indicates that a nucleotide sequence of interest is linked to regulatory sequences such that expression of the nucleotide sequence is achieved.

Vectors can be divided into two general classes: Cloning vectors are replicating plasmid or phage with regions that are non-essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors, or tissue-specific promoters. Vectors have many manifestations. A "plasmid" is a circular double stranded DNA molecule that can accept additional DNA fragments. Viral vectors can also accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) integrate into the genome of a host cell and replicate as part of the host genome. In general, useful expression vectors are plasmids and viral vectors (e.g., replication defective retroviruses, adenoviruses and adeno-associated viruses); other expression vectors can also be used.

Vectors can be introduced in a variety of organisms and/or cells (Table D). Alternatively, the vectors can be transcribed and translated in vitro, for example using T7 promoter regulatory sequences and T7 polymerase.

TABLE D

Examples of hosts for cloning or expression

| Organisms | Examples | Sources and References* |
|---|---|---|
| Prokaryotes | | |
| Enterobacteriaceae | E. coli | |
| | K 12 strain MM294 | ATCC 31,446 |
| | X1776 | ATCC 31,537 |
| | W3110 | ATCC 27,325 |
| | K5 772 | ATCC 53,635 |
| | Enterobacter | |
| | Erwinia | |
| | Klebsiella | |
| | Proteus | |
| | Salmonella (S. tyhpimurium) | |
| | Serratia (S. marcescans) | |
| | Shigella | |
| | Bacilli (B. subtilis and B. licheniformis) | |
| | Pseudomonas (P. aeruginosa) | |
| | Streptomyces | |
| Eukaryotes | | |
| Yeasts | Saccharomyces cerevisiae | |
| | Schizosaccharomyces pombe | |
| | Kluyveromyces | (Fleer et al., 1991) |
| | K. lactis MW98-8C, CBS683, CBS4574 | (de Louvencourt et al., 1983) |
| | K. fragilis | ATCC 12,424 |
| | K. bulgaricus | ATCC 16,045 |
| | K. wickeramii | ATCC 24,178 |
| | K. waltii | ATCC 56,500 |
| | K. drosophilarum | ATCC 36,906 |
| | K. thermotolerans | |
| | K. marxianus; yarrowia | (EPO 402226, 1990) |
| | Pichia pastoris | (Sreekrishna et al., 1988) |
| | Candida | |
| | Trichoderma reesia | |
| | Neurospora crassa | (Case et al., 1979) |
| | Torulopsis | |
| | Rhodotorula | |
| | Schwanniomyces (S. occidentalis) | |

TABLE D-continued

Examples of hosts for cloning or expression

| Organisms | Examples | Sources and References* |
|---|---|---|
| Filamentous Fungi | Neurospora Penicillium Tolypocladium Aspergillus (A. nidulans and A. niger) | (WO 91/00357, 1991) (Kelly and Hynes, 1985; Tilburn et al., 1983; Yelton et al., 1984) |
| Invertebrate cells | Drosophila S2 Spodoptera Sf9 | |
| Vertebrate cells | Chinese Hamster Ovary (CHO) simian COS COS-7 HEK 293 | ATCC CRL 1651 |

*Unreferenced cells are generally available from American Type Culture Collection (Manassas, VA).

Vector choice is dictated by the organism or cells being used, and the desired fate of the vector. Vectors may replicate once in the target cells or may be "suicide" vectors. In general, vectors comprise signal sequences, origins of replication, marker genes, enhancer elements, promoters, and transcription termination sequences. The choice of these elements depends on the organisms in which the vector will be used. Some of these elements may be conditional, such as an inducible or conditional promoter that is turned "on" when conditions are appropriate. Examples of inducible promoters include those that are tissue-specific, which relegate expression to certain cell types, steroid-responsive, or heat-shock reactive. Some bacterial repression systems, such as the lac operon, have been exploited in mammalian cells and transgenic animals (Fieck et al., 1992; Wyborski et al., 1996; Wyborski and Short, 1991). Vectors often use a selectable marker to facilitate identifying those cells that have incorporated the vector. Many selectable markers are well known in the art for use with prokaryotes, usually antibiotic-resistance genes or the use of autotrophy and auxotrophy mutants. Table F summarizes many of the available markers.

Methods of eukaryotic cell transfection and prokaryotic cell transformation are well known in the art. The choice of host cell dictates the preferred technique for introducing the nucleic acid of interest. For mammalian cells, transfection techniques that are exceptionally useful include, e.g., calcium phosphate precipitation-mediated transfection, liposomes, viruses, and electroporation.

Screening Assays

The invention provides a method (screening assay) for identifying modalities, i.e., candidate or test compounds or agents (e.g., peptides, peptidomimetics, small molecules or other drugs), foods, combinations thereof, etc., that effect neuronal functions, whether stimulatory or inhibitory, including gene expression and translation, gene activity or copies of the gene in cells. The invention also provides a method for testing for compounds that increase or decrease the neurological effect or neuronal activity, such as increasing or decreasing the formation of neurotransmitters (e.g., dopamine, serotonin or acetylcholine), neurotransmitter receptors, transmitter binding or even cell death. Differentiation factors may be applied to the cells before contacting the cells with a compound. A compound may modulate neurological effects by affecting: (1) the number of copies of at least one gene in the cell (amplifiers and deamplifiers); (2) increasing or decreasing the transcription of at least one gene (transcription up-regulators and down-regulators); (3) by increasing or decreasing the translation of at least one mRNA into polypeptide (translation up-regulators and down-regulators); or (4) by increasing or decreasing the activity of at least one polypeptide itself (agonists and antagonists). Genes, mRNAs and polypeptides that are especially useful to observe include those for neurotransmitters and their receptors (such as variations of their expression or activity).

(a) Effects of Compounds

To identify compounds that affect neurological function, the cells of the invention are contacted with a candidate compound, and the corresponding change in the target polypeptide is assessed (Ausubel et al., 1987). For DNA amplifiers and deamplifiers, the amount of a target gene, such as one that encodes a neurotransmitter, is measured; for those compounds that are transcription up-regulators and down-regulators, the amount of a target mRNA is determined; for translational up- and down-regulators, the amount of a target polypeptide is measured. Compounds that are agonists or antagonists may be identified by contacting cells with the compound.

(b) Small Molecules

A "small molecule" refers to a composition that has a molecular weight of less than about 5 kD and more preferably less than about 4 kD, and most preferably less than 0.6 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention. Examples of methods for the synthesis of molecular libraries are described (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or phage (Cwirla et al., 1990; Devlin et al., 1990; Felici et al., 1991; Ladner et al., U.S. Pat. No. 5,223,409, 1993; Scott and Smith, 1990).

(c) Screens to Identify Modulators

Modulators of the expression of a polypeptide can be identified in a method where a cell is contacted with a candidate compound and the expression of the polypeptide mRNA or polypeptide in the cell is determined. The expression level of the polypeptide mRNA or polypeptide in the presence of the candidate compound is compared to the polypeptide mRNA or polypeptide levels in the absence of the candidate compound. The candidate compound can then be identified as a modulator of the polypeptide mRNA or polypeptide expression based upon this comparison. For example, when expression of the polypeptide mRNA or polypeptide is greater (i.e., statistically significant) in the presence of the candidate compound than in its absence, the candidate compound is identified as a stimulator of that polypeptide mRNA or polypeptide expression. Alternatively, when expression of the polypeptide mRNA or polypeptide is less (statistically significant) in the presence of the candidate compound than in its absence, the candidate compound is identified as an inhibitor of the polypeptide mRNA or polypeptide expression. The level of the polypeptide mRNA or polypeptide expression in cells can be determined by methods described for detecting polypeptide mRNA or polypeptide.

VIII. Identifying Markers Associated with a Neurological Disorder

In another aspect, the cells of the invention may be used to identify markers that are associated with a neurological disease or disorder. Such markers include, for example, gene expression difference and genetic lesions. One useful approach would include identifying those genes that are differentially expressed between those stem cells of the invention isolated from a healthy individual and those isolated from an individual afflicted with a neurological disorder. Many methods are available in the art to determine differential gene expression (Ausubel, 1987). Especially useful are those methods that take advantage of high-throughput formats, such as gene chips.

Genetic lesions can be detected by ascertaining: (1) a deletion of one or more nucleotides from a target polypeptide gene; (2) an addition of one or more nucleotides to the target polypeptide gene; (3) a substitution of one or more nucleotides in the target polypeptide gene (4) a chromosomal rearrangement of a gene; (5) an alteration in the level of mRNA transcripts, (6) aberrant modification of the target polypeptide, such as a change genomic DNA methylation, (7) the presence of a non-wild-type splicing pattern of a target mRNA transcript, (8) a non-wild-type level of the target polypeptide gene, (9) allelic loss of the target polypeptide gene, and/or (10) inappropriate post-translational modification of the polypeptide. Mutations in a target polypeptide from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicate mutations in the sample DNA. Moreover, the use of sequence specific ribozymes can be used to score for the presence of specific mutations by development or loss of a ribozyme cleavage site.

Hybridizing sample and control nucleic acids, e.g., DNA or RNA, to high-density arrays containing hundreds or thousands of oligonucleotide probes, can identify genetic mutations in a target polypeptide (Cronin et al., 1996; Kozal et al., 1996). For example, genetic mutations in a target polypeptide can be identified in two-dimensional arrays containing light-generated DNA probes (Cronin et al., 1996). Briefly, a first hybridization array of probes can be used to scan through long stretches of DNA in a sample and control to identify base changes between the sequences by making linear arrays of sequential overlapping probes. This step allows the identification of point mutations. A second hybridization array follows that allows the characterization of specific mutations by using smaller, specialized probe arrays complementary to all variants or mutations detected. Each mutation array is composed of parallel probe sets, one complementary to the wild-type gene and the other complementary to the mutant gene.

Other methods for detecting mutations in a target polypeptide include those in which protection from cleavage agents is used to detect mismatched bases in RNA/RNA or RNA/DNA heteroduplexes (Myers et al., 1985). In general, the technique of "mismatch cleavage" starts by providing heteroduplexes formed by hybridizing (labeled) RNA or DNA containing the wild-type target polypeptide sequence with potentially mutant RNA or DNA obtained from a sample. The double-stranded duplexes are treated with an agent that cleaves single-stranded regions of the duplex such as those that arise from base pair mismatches between the control and sample strands. For instance, RNA/DNA duplexes can be treated with RNase and DNA/DNA hybrids treated with $S_1$ nuclease to enzymatically digest mismatched regions. In other embodiments, either DNA/DNA or RNA/DNA duplexes can be treated with hydroxylamine or osmium tetroxide and with piperidine in order to digest mismatched regions. The digested material is then separated by size on denaturing polyacrylamide gels to determine the mutation site (Grompe et al., 1989; Saleeba and Cotton, 1993). The control DNA or RNA can be labeled for detection.

Mismatch cleavage reactions may employ one or more polypeptides that recognize mismatched base pairs in double-stranded DNA (DNA mismatch repair) in defined systems for detecting and mapping point mutations in a target polypeptide cDNA obtained from samples of cells. For example, the mutY enzyme of *E. coli* cleaves A at G/A mismatches and the thymidine DNA glycosylase from HeLa cells cleaves Tat G/T mismatches (Hsu et al., 1994). The duplex is treated with a DNA mismatch repair enzyme, and the cleavage products, if any, can be detected from electrophoresis protocols or the like (Modrich et al., U.S. Pat. No. 5,459,039, 1995).

Electrophoretic mobility alterations can be used to identify mutations in a target gene. For example, single strand conformation polymorphism (SSCP) may be used to detect differences in electrophoretic mobility between mutant and wild type nucleic acids (Cotton, 1993; Hayashi, 1992; Orita et al., 1989). Single-stranded DNA fragments of sample and control nucleic acids are denatured and then renatured. The secondary structure of single-stranded nucleic acids varies according to sequence; the resulting alteration in electrophoretic mobility allows detection of even a single base change. The DNA fragments may be labeled or detected with labeled probes. Assay sensitivity can be enhanced by using RNA (rather than DNA), in which the secondary structure is more sensitive to sequence changes. The method may use heteroduplex analysis to separate double stranded heteroduplex molecules on the basis of changes in electrophoretic mobility (Keen et al., 1991).

The migration of mutant or wild-type fragments can be assayed using denaturing gradient gel electrophoresis (DGGE; (Myers et al., 1985). In DGGE, DNA is modified to prevent complete denaturation, for example by adding a GC clamp of approximately 40 by of high-melting point, GC-rich DNA by PCR. A temperature gradient may also be used in place of a denaturing gradient to identify differences in the mobility of control and sample DNA (Rossiter and Caskey, 1990).

Examples of other techniques for detecting point mutations include selective oligonucleotide hybridization, selective amplification, or selective primer extension. For example, oligonucleotide primers can be prepared in which the known mutation is placed centrally and then hybridized to target DNA under conditions that permit hybridization only if a perfect match is found (Saiki et al., 1986; Saiki et al., 1989). Such allele-specific oligonucleotides are hybridized to PCR-amplified target DNA or a number of different mutations when the oligonucleotides are attached to the hybridizing membrane and hybridized with labeled target DNA.

Alternatively, allele specific amplification technology that depends on selective PCR amplification may be used. Oligonucleotide primers for specific amplifications may carry the mutation of interest in the center of the molecule (so that amplification depends on differential hybridization (Gibbs et al., 1989)) or at the extreme 3'-terminus of one primer where, under appropriate conditions, mismatch can prevent, or reduce polymerase extension (Prosser, 1993). Novel restriction sites in the region of the mutation may be introduced to create cleavage-based detection (Gasparini et al., 1992).

Amplification may also be performed using Taq ligase (Barany, 1991). In such cases, ligation occurs only if there is a perfect match at the 3'-terminus of the 5' sequence, allowing detection of a known mutation by scoring for amplification.

Another aspect of the invention provides methods for determining neurological polypeptide activity or nucleic acid expression in an individual to select appropriate therapeutic or prophylactic agents specifically for that individual (pharmacogenomics). The invention provides an exceptionally powerful tool in that large numbers of cells from patients can be grown in vitro and then, if desired, induced to differentiate into the cell type in which the disease or disorder is manifested. Pharmacogenomics allows for the selection of modalities (e.g., drugs, foods) for therapeutic or prophylactic treatment of an individual based on the individual's genotype (e.g., the individual's genotype to determine the individual's ability to respond to a particular agent). Another aspect of the invention pertains to monitoring the influence of modalities (e.g., drugs, foods) on the expression or activity of the neurological polypeptide in clinical trials.

Diagnostic Assays

An exemplary method for detecting the presence or absence of a target polypeptide in a biological sample involves obtaining a biological sample from a subject and contacting the biological sample with a compound or an agent capable of detecting the polypeptide or nucleic acid such that the presence of the polypeptide is confirmed in the sample. An agent for detecting a polypeptide message or DNA is a labeled nucleic acid probe that specifically hybridizes the target mRNA or genomic DNA. An agent for detecting a polypeptide may be an antibody, preferably an antibody with a detectable label. Abs can be polyclonal, or more preferably, monoclonal. An intact antibody, or a fragment (e.g., $F_{ab}$ or $F_{(ab')2}$) can be used.

Prognostic Assays

Diagnostic methods can furthermore be used to identify subjects having, or at risk of developing, a disease or disorder associated with aberrant polypeptide expression or activity, such as obesity or obesity-related complications. Prognostic assays can be used to identify a subject having or at risk for developing a disease or disorder. A method for identifying a disease or disorder associated with aberrant polypeptide expression or activity would include a test sample obtained from a subject and detecting a polypeptide or nucleic acid (e.g., mRNA, genomic DNA). A test sample is a biological sample obtained from a subject. For example, a test sample can be a biological fluid (e.g., serum), cell sample, or tissue.

Prognostic assays can be used to determine whether a subject can be administered a modality (e.g., an agonist, antagonist, peptidomimetic, polypeptide, peptide, nucleic acid, small molecule, food, etc.) to treat a disease or disorder associated with aberrant polypeptide expression or activity. Such methods can be used to determine whether a subject can be effectively treated with an agent for a disorder, such as Parkinson's disease. Methods for determining whether a subject can be effectively treated with an agent include obtaining olfactory stem cells from a patient and detecting a target polypeptide or nucleic acid (e.g., where the presence of the polypeptide or nucleic acid is diagnostic for a subject that can be administered the agent to treat a disorder associated with aberrant polypeptide expression or activity). The isolated stem cells may be treated with one or more differentiation factors before assaying for the polypeptide or nucleic acid presence or activity.

Genetic lesions in a target polypeptide can be used to determine if a subject is at risk for a disorder, such as Parkinson's disease. Methods include detecting, in olfactory stem cells (or differentiated cells arising from the olfactory stem cells) from the subject, the presence or absence of a genetic lesion characterized by an alteration affecting the integrity of a gene encoding the target polypeptide or the mis-expression of the target polypeptide.

IX. Cultures and Kits for Testing Pharmaceutical Compounds

The stem cell of the present invention may be obtained from donors with unique neurodegenerative disorders, such as bi-polar disorder, multiple sclerosis or amyotrophic lateral sclerosis. An ONe stem cell may be isolated from a donor, including a cadaver, or from a donor with a unique neurodegenerative disorder. Neurological stem cells of the donor can be maintained in culture, and can give rise to a population of either differentiated or undifferentiated cells that would be useful in testing and developing pharmaceutical compounds as treatments for any diseases or that unique disease of the donor. These cells can be included in a kit, container, pack or dispenser together with instructions for use. When the invention is sold as a kit, the ONe stem cells may also be frozen and then thawed immediately before use. Freezing may permit long-term storage without losing the stem cell function.

Potential drug candidates may be contacted with the stem cell or the differentiated progeny and then the cell examined for changes such as increased or decreased expression of proteins.

(a) Containers or Vessels

Standard cell freezing conditions may be determined based on the cell type. A common method is 0.5%-20% Dimethyl Sulfoxide (DMSO), and preferably 10% DMSO and more preferably 5% DMSO (or some other salt capable of inhibiting ice crystal formation) in either 100% serum, cell media or cell media without serum. Cells are carefully collected, washed, concentrated to a suitable density (generally a high density), and then placed in vials. Cells are then placed in an insulated container (e.g. a Styrofoam box) and placed at −20° C. in a freezer for 3 hours to a week, or even longer, when necessary or desirable. Next, the cells are transferred to liquid nitrogen for permanent storage. Cells may be shipped on dry ice.

To re-initiate the culture, the cells are usually defrosted rapidly and placed immediately into pre-warmed culture media.

(b) Instructional Materials ¶90. Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

It should be appreciated by those of skill in the art that the techniques disclosed in the examples that follow represent the techniques discovered by the inventors to function well in the practice of the invention, and thus can be considered to constitute possible modes for its practice. However, those of skill in the art should, in light of the present disclosure, appreciate that many changes can be made in the specific embodiments that are disclosed and still obtain a like or similar result without departing from the spirit and scope of the invention.

A. Primary Cell Cultures from Human Cadavers

A lateral rhinotomy approach was employed to remove the olfactory mucosa from underlying tissues from 4 to 18 hour postmortem cadavers. The tissue was then harvested into a cold solution of 0.05% trypsin in $Ca^{2+}$ and $Mg^{2+}$ free Hank's balanced salt solution (HBSS; GIBCO, Grand Island, N.Y.). ONe was removed from its supporting tissues by micro-dissection in cold HBSS, minced into 1 $mm^3$ pieces, and washed repeatedly with several changes of fresh HBSS. After resuspension in HBSS containing 0.05% trypsin followed by 4 washes with 0.01% deoxyribonuclease in $Ca^{2+}$ and $Mg^{2+}$ free HBSS, cells were incubated for 90 minutes at 37° C. with gentle $O_2$ bubbling to allow dissociation. The tissue and individual cells were centrifuged; the pellet was dispersed by trituration through a fire polished Pasteur pipette and resuspended in growth medium consisting of DMEM and F12 (1:1) and 10% heat-inactivate fetal bovine serum (FBS) (all media components from GIBCO, Grand Island, N.Y.). The cells were plated on laminin-fibronectin coated plastic plates, incubated in an atmosphere of 5% $CO_2$ in air, and fed every 3-4 days.

B. Subcultures for Immunofluorescense

Cells were plated at a concentration of $4\times10^4$ cells/well on 22 mm diameter, prewashed, uncoated coverslips in olfactory epithelial medium (OEM) which consists of 90% Minimal Essential Medium with Hanks' salts with L-glutamine, 10% FBS, and 1 ml of 10 mg/dl gentamycin and incubated for a minimum of 2 days at 37° C. in an atmosphere of humidified 5% $CO_2$ in air to allow attachment prior to immunolocalization.

C. Immunofluorescent Localization

Cultures were rinsed with cytoskeletal buffer (CB): MES (2-[N-Morpholino]ethane sulfonic acid), 1.95 mg/ml; NaCl, 8.76 mg/ml; 5 mM EGTA; 5 mM $MgCl_2$; glucose, 0.9 mg/ml, pH 6.1) and fixed for 10 min at room temperature with 3% paraformaldehyde in CB. Cells were permeabilized with 0.2% Triton X-100 (SIGMA, St. Louis, Mo.) or cold acetone (preferably about 4° C.), for 10 minutes at room temperature. Nonspecific binding sites were blocked by a 1 hour treatment with 1% bovine serum albumin (BSA) in Tris-Buffered Saline (TBS): Tris, 2.42 mg/ml; NaCl, 8.9 mg/ml; 2 mM EGTA; 2 mM MgCl; pH 7.5. To facilitate identification of unreactive cells, 4'6-diaminidino-2-phenylindole dihydrochloride (DAPI): 1:500; 2 mg/ml (Molecular Probes, Eugene, Oreg.) was used to vitally stain DNA in each cell, after which the cells were incubated overnight at 4° C. with the primary antibodies listed in Table 1.

After extensive washing with TBS, the cells on the coverslips were incubated for 1 hour at 37° C. with the following secondary antibodies: fluorescein-conjugated goat anti-mouse IgG, fluorescein-conjugated goat anti-rabbit IgG, Texas-red-conjugated goat anti-mouse IgG, Texas-red-conjugated goat anti-rabbit IgG (all diluted 1:40, FITC from Cappel, West Chester, Pa.; Texas Red from Molecular Probes, Eugene, Oreg.). The immunohistochemical procedures were established in our laboratory. Preabsorbed and secondary antibody only (omission) controls insured the specificity of the reaction. The rat NGF-responsive pheochromocytoma cell line (PC12; American Type Tissue Culture Collection; Manassas, Ohio) was used as the positive control for the low affinity receptor $p75^{NGFr}$ and Trk antibodies. The 3T3 fibroblast line was used as a negative control. Coverslips were mounted with Mowiol 4-88 (HOECHST CELANESE, Sommerville, N.J.) and observed with fluorescence optics using the Leica 4d confocal microscope equipped with argon/krypton and UV lasers. To facilitate direct comparison of treatments, all photomultiplier voltages were kept constant during individual experiments. Confocal images representing 1 μm optical sections were digitized to 1024×1024 pixels and presented as maximum density projections.

D. Electron Microscopy

Tissue sections were washed with pH 7.4 cacodylate buffer, fixed for 1 hour in 2.5% glutaraldehyde in 0.1 M cacodylate buffer, postfixed for 30 minutes in 1% osmium tetroxide in cacodylate buffer, dehydrated through a graded series of ethanols followed by propylene oxide, and embedded in LX-112 (ELECTRON MICROSCOPY SCIENCES, Ft. Washington, Pa.). The blocks were trimmed and thick and thin sections were cut and stained with uranyl acetate and lead citrate prior to examination in a Philips CM10 or CM12 transmission electron microscope.

E. cAMP

An analysis of the effects of cAMP on neurosphere subcultures increases the understanding of what trophic agents might be involved. Cell cultures were plated at identical densities ($4\times10^4$ cells/well) and maintained in olfactory epithelial medium (OEM; 90% Minimal Essential Medium with Hanks' salts with L-glutamine, 10% FBS, and 1 ml of 10 mg/dl gentamycin) for 72 hours and in OEM supplemented with 2.5 mM dibutyrl-cAMP. Cultures were processed for immunofluorescence using antibodies against actin, β-tubulin isotype III, and α-internexin. Within 24 hours of cAMP addition to the cultures, fewer mitotic figures were seen per field and process formation occurred. CAMP reduced cell division and increased process formation. The lineage restriction and differentiation produced by 24 hour exposure to dibutyrl-cAMP demonstrates that some ONe neurosphere forming cells retain the ability to form neuroblasts.

F. MTT Assay

A commercial assay (SIGMA, St. Louis, Mo.) was used to evaluate cell viability by assessing the reduction of MTT (3-[4,5-dimethylthiazol-2-yl]-2,5-diphenyl tetrazoluim bromide) by mitochondrial dehydrogenase present in viable cells. An increase in the value of the MTT corresponded to an increase in the cell number. Cells were plated at a density of $1\times10^5$ cells/well. After incubation at 37° C. for 24 hours, MTT equal to 10% of the culture volume was added to each well. Plates were incubated at 37° C. for an additional 4 hours and processed as directed by the manufacturer. The MTT assay of cell viability was used to determine if viability remained constant through various passages. No significant differences (significance was set at $P<0.05$ using ANOVA) were detected.

G. Results

ONe harvested 4-18 hours postmortem exhibited a high level of ultrastructural integrity. The olfactory vesicles (OV) with intact non-motile kinocilia were seen. Adjacent cells with motile (9+2) cilia were packed with apical mitochondria and formed tight junctions with ORNs, reflecting their common epithelial origin. Within the first week of culture, most of the viable cells attached to the surface and assumed bipolar, fusiform, stellate or spherical shapes. The heterogeneous population included ORNs, OECs, epithelial supporting cells, fibroblasts and pluripotent cells. The presence of four specific cell types was confirmed by immunolocalization of lineage-specific antigens and by ultrastructural analysis. ORNs were identified by their neurofilaments and microtubules composed of β-tubulin isotype III that extended throughout their processes as well as the presence of MAP2ab.

Keratin-negative OECs were frequently so closely associated with the ORNs that at times their cell boundaries could be detected only by electron microscopy boundaries. The epithelial supportive population consisted of highly flattened, contact inhibited keratin-positive cells that formed monolayer nests.

ORNs and OECs became vacuolated, retracted their processes and died after the third week in vitro. In approximately 5-10% of the cultures, a population of mitotically active cells emerged. These cells doubled every day, were poorly adherent, and appeared to grow in semi-suspension. They were allowed to proliferate undisturbed for an additional 2 weeks during which they formed spheres composed of approximately 20-80 cells (FIG. 1). The initial plating density did not alter the time in vitro required for sphere formation. The few cells not associated directly with a specific sphere usually appeared in pairs. The spheres were collected and mechanically dispersed into individual cells, repeatedly washed and centrifuged to remove cell debris. These cultures have been maintained for approximately twenty months and have been through approximately 200 passages.

Figure 2:
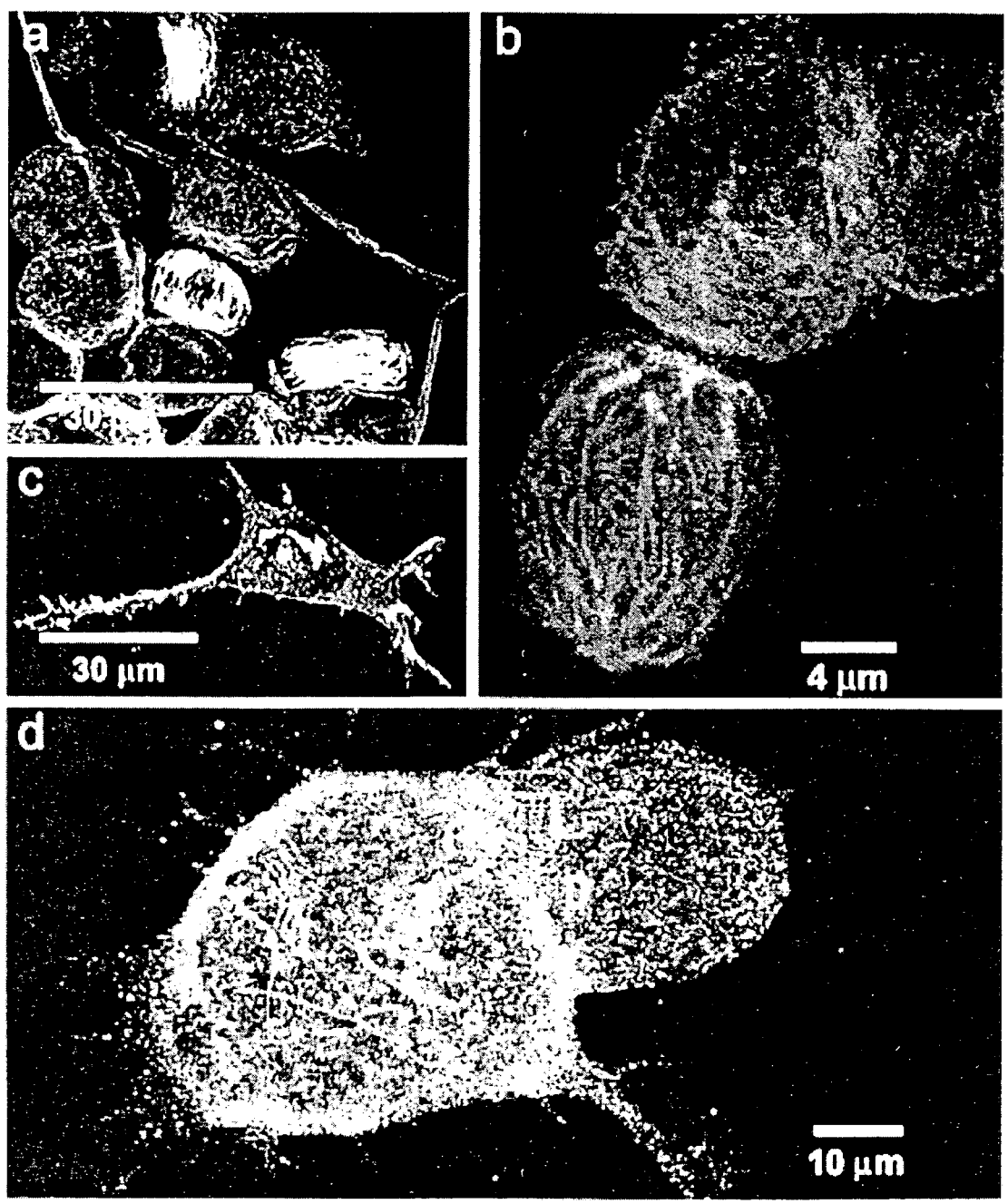
FIG. 2a-2b. Neurosphere forming cells immunopositive for β-tubulin isotype III.
FIG. 2c. Neurosphere forming cells immunopositive for NCAM.
FIG. 2d. Neurosphere forming cells immunopositive for MAP2ab

Cells were probed with lineage-specific antibodies after several passages (FIG. 2). The majority of the cells were positive for one or more of the following neuronal makers: β-tubulin isotype III, NCAM and MAP2ab (FIG. 2). A complex neuron-specific microtubular network was evident even in mitotically active cells. NCAM-positive fluorescence was detected on spinous projections along the processes of cells that assumed bipolar or multipolar shapes (FIG. 2). MAP2ab was localized in doughnut-like structures and short linear segments (FIG. 2).

Figure 3:
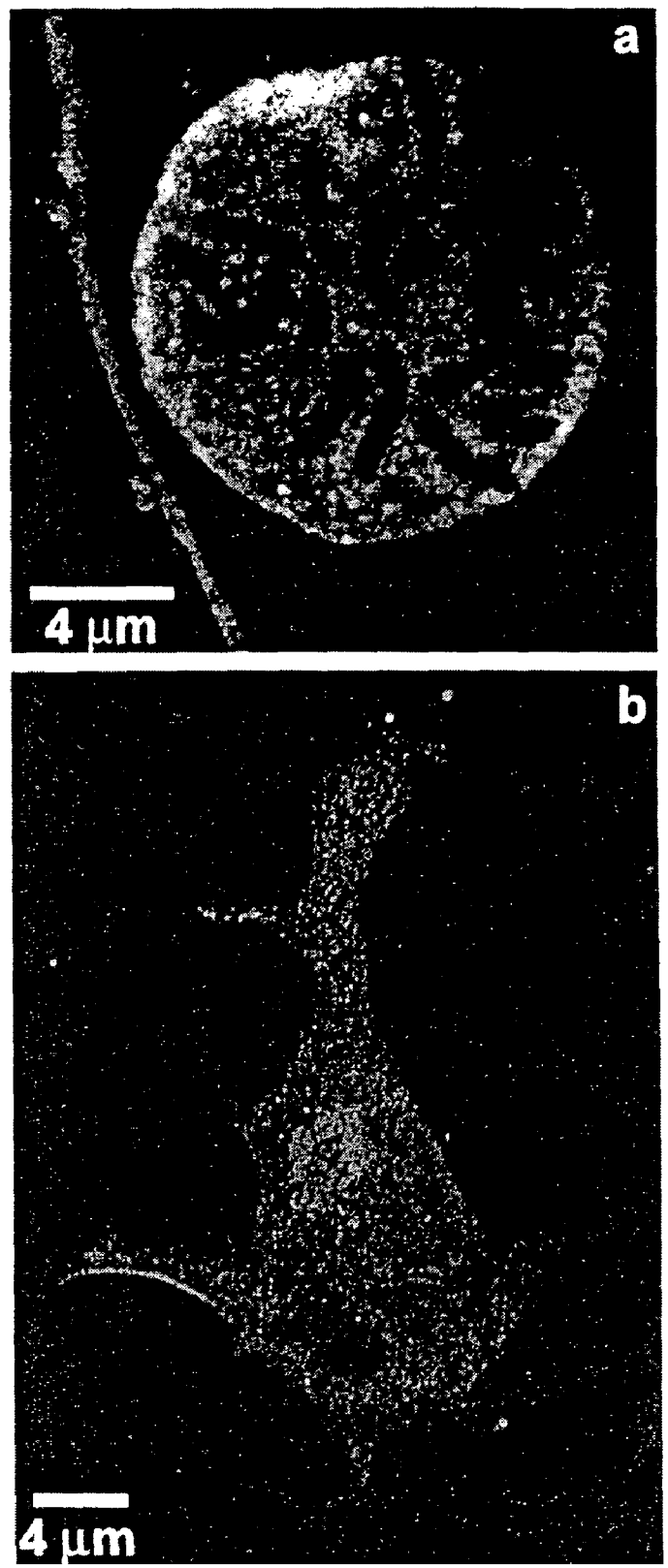
FIG. 3a-3b. Neurosphere cells immunonegative for neuronal markers β-tubulin isotype III, NCAM, and MAP2ab, but immunopositive for A2B5 and GFAP.

Approximately 10% of the cells were negative for all of the neuronal markers evaluated. Some of the neuronal negative cells were immunoreactive with A2B5 (mAb reacted with an FITC component), an antibody against a ganglioside-enriched in glial membranes, and/or GFAP (pAb which was reacted with Texas red) as demonstrated by double labeled experiments. (FIG. 3a) Most of these cells appeared to be in mitosis. The fluorescent material was punctate and distributed on the cell surface and in the perikaryal cytoplasm. Occasionally in well-spread cells, highly concentrated GFAP reactivity was observed arranged in a perinuclear circular array of globular fluorescence (FIG. 3b). No cells were found positive for RIP or Nestin. Furthermore cells subcultured from neurospheres were unreactive with either a polyclonal antibody against keratin or a monoclonal antibody against cytokeratins 5/6. All immunological results remained similar for more than 200 passages.

Figure 4:
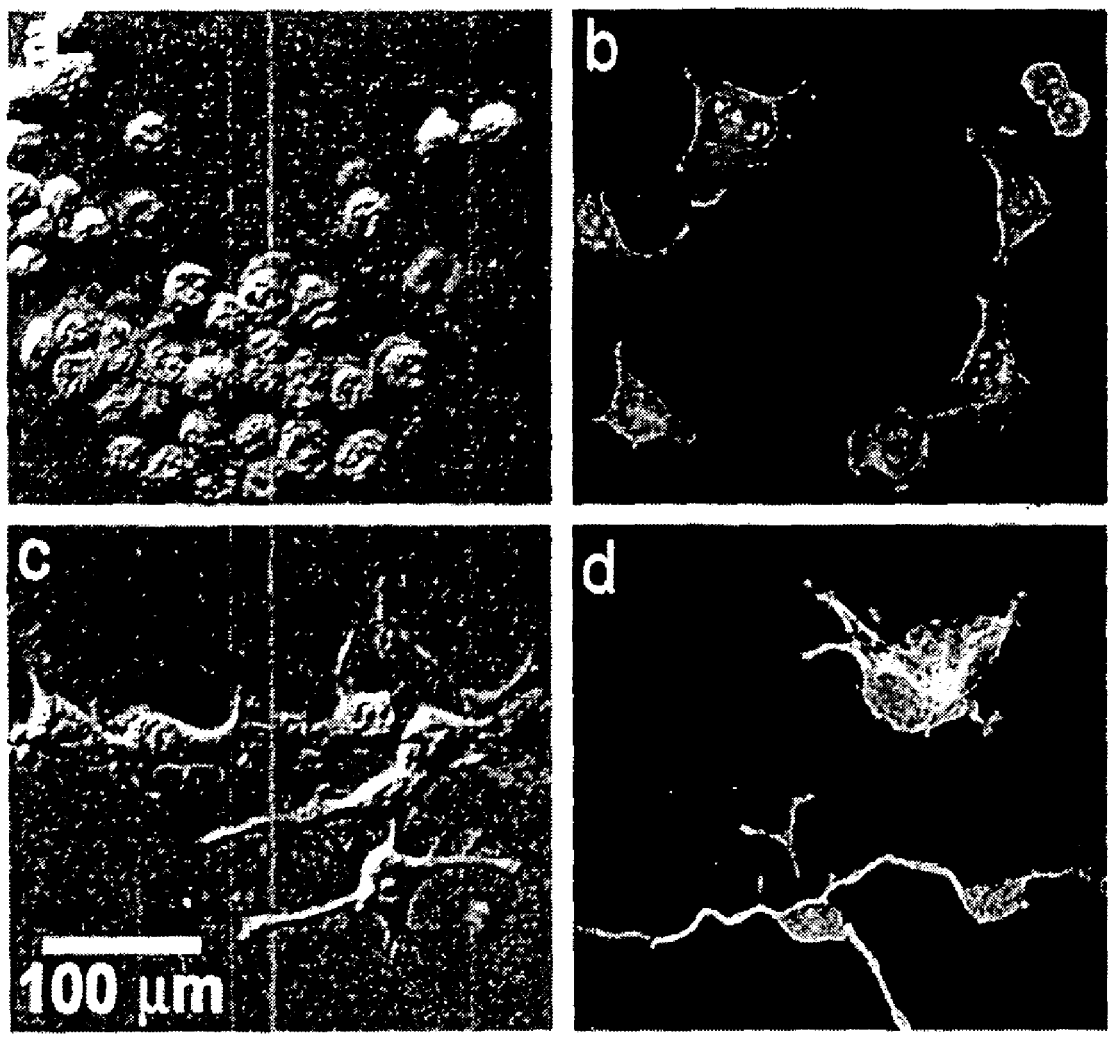
FIG. 4a-4b. Subculture of neurosphere-forming cells.
FIG. 4c-4d. Subculture of neurosphere-forming cells supplemented with 2.5 mM dibutyryl-cAMP.

Approximately 24 hours after exposure to dibutyryl cAMP, fewer mitotic neurospheres were seen and process formation occurred. The addition of dibutyryl cAMP reduced cell division and increased process formation. FIGS. 4a and 4c were taken with Nomarski optics. Bipolar and multipolar cells with 40 μM long β-tubulin III positive processes formed after 72 hours. (FIG. 4). Alpha-internexin, a neuronal marker that appears prior to neurofilament formation in developing neurons was localized in an occasional process bearing cell. In contrast, cultures maintained in the absence of the nucleotide or sodium butyrate (5 mM) remained highly mitotic, had minimal neuritogenesis, and were negative for α-internexin.

The MTT assay of cell viability was used to determine if viability remained constant through various passages. No significant differences (P<0.05) were detected.

Figure 5:
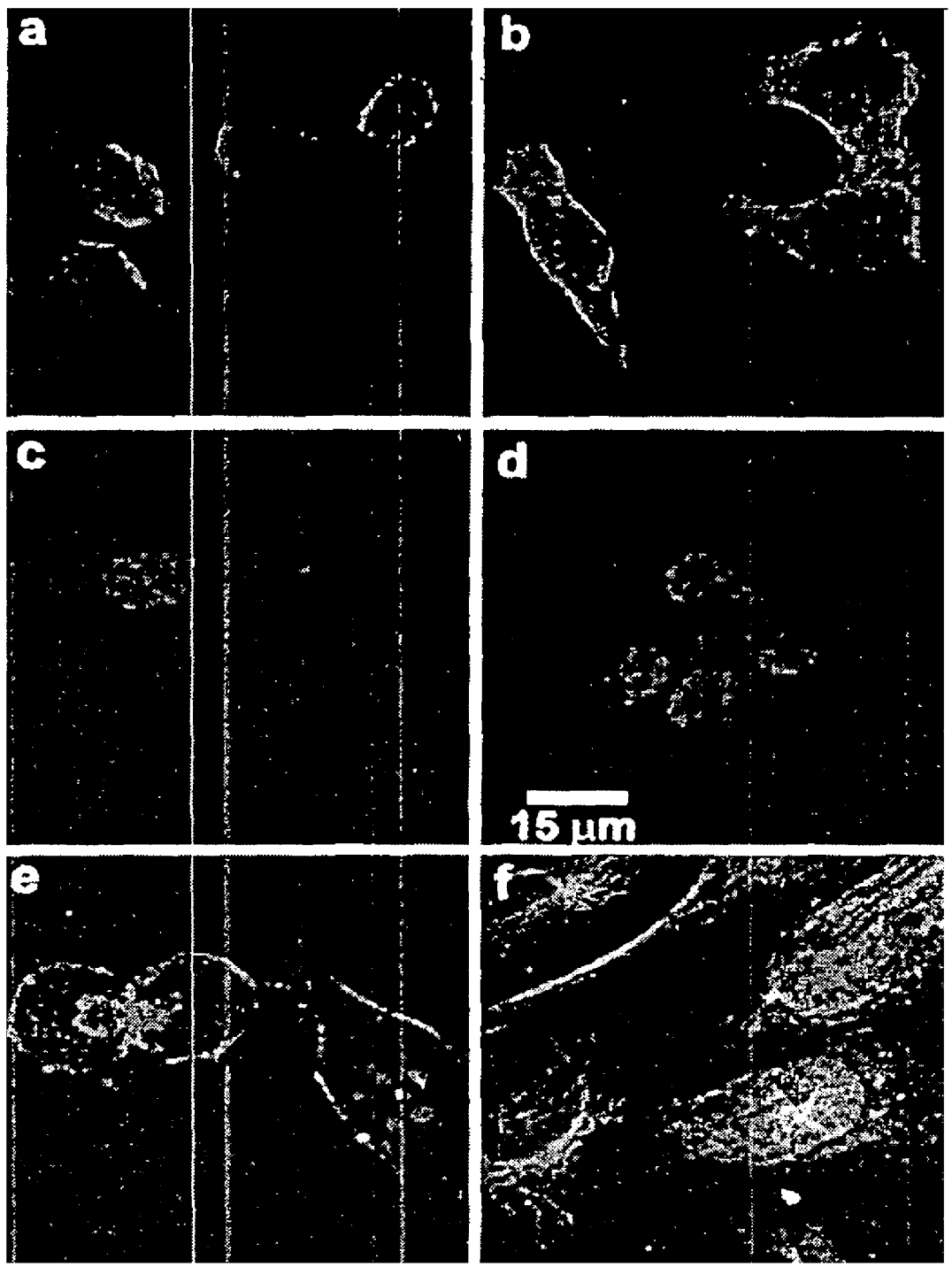
FIG. 5. Localization of Trk receptors on subcultured neurosphere-forming cells.

The nature of neurosphere forming cells was characterized further by determining the presence and distribution of a family of neurotrophin receptor kinases (Trk A, B, C, and pan). The majority of the cells were reactive for Trk A and B, but negative for Trk C. Trk A is restricted to a small population of basal cells until its acceleration by bulbectomy. Trk B is widely distributed in immature neurons and becomes more abundant as the neurons mature following target innervation. Trk C is present only in highly differentiated ORNs. Occasionally, cells were observed that were positive solely for Trk A or B, while a smaller population remained immunonegative for all Trks, including a monoclonal antibody that recognized all three. Trk A had the most intense immunoreactivity. Under conditions of low serum (<2%), Trk A immunoreactivity occurred in patches which in some cells aggregated to form polar caps (FIG. 5). In contrast, punctate Trk B immunoreactivity was distributed over the entire surface and extended to the distal regions of the processes (FIG. 5). The neurosphere forming population was further probed with antibody for the human low affinity NGF receptor $p75^{NGFr}$ (FIG. 5). No positive cells were observed. Double-labeling demonstrated the absence of $p75^{NGFr}$ immunoreactivity even in Trk A positive cells (FIG. 5). The 3T3 fibroblasts served as a negative control for Trk A.

Further, though the default phenotype of the human olfactory stem cell is typically neuronal, the cells also occasionally exhibited glial and epithelial expression. B104 cells (BCM) are known to promote oligoprogenitors and produce "oligospheres" (V. Avellana-Adalid, et. al., 1996), in non-human cells (i.e. it has been shown to have this property in mice) and was therefore added to the ONe neurosphere culture media. BCM exposure resulted in oligosphere-like formation within 72 hours and the effect was dose dependent. The cells were oligosphere-like because they showed an increased level of cells immunopositive for A2B5, a glial and oligodendrocyte marker.

J. Prophetic Examples

1. Treatment of Parkinson's Disease

Initially, obtain ONe tissue from either the patient suffering from Parkinson's disease, or from a histocompatible donor. Preferably the donor is related to the patient, and more preferably the donor is an immediate relative of the patient. Preferably the ONe tissue is obtained through an endoscopic bioposy.

Next grow the ONe tissue in culture and isolate neurospheres from the culture. Optionally, dibutyryl cAMP, various substrata, and neurotrophic growth factors may be added to initiate differentiation of the neurosphere cells.

The cells may then be transplanted, for example, by injecting them into the Substantia Nigra of the brain. Once the neurons are present in the brain of the afflicted individual, they will produce dopamine, and thereby help treat the disease. One advantage of this method is that it may be repeated, as needed, and thereby alleviate some of the suffering of the patient. Optionally, cells may be selected for the excretion of dopamine before transplantation. Optionally, cells may be differentiated prior to transplantation.

2. Treatment of Multiple Sclerosis

Initially, obtain ONe tissue from either the patient suffering from multiple sclerosis, or from a histocompatible donor. Preferably the donor is related to the patient, and more preferably the donor is an immediate relative of the patient. Preferably the ONe tissue is obtained through an endoscopic biopsy.

Next grow the ONe tissue in culture and isolate oligosphere-like cells from the culture. Optionally, dibutyryl cAMP and growth factors may be added to initiate differentiation of the oligosphere-like cells.

The cells may then be transplanted, for example, by injecting them into the spinal cord, brain or other such area having a patch of sclerosis. Once the transplanted cells are present in the afflicted individual, they will produce myelin, and thereby help treat the disease. One advantage of this method is that it may be repeated, as needed, and thereby alleviate some of the suffering of the patient. Optionally, cells may be selected for the production of myelin before transplantation. Optionally, cells may be differentiated prior to transplantation.

REFERENCES

EPO 402226. 1990. Transformation vectors for yeast *Yarrowia*.

D. R. Archer, P. A. Cuddon, D. Libsitz, L. D. Duncan. 1997. Myelination of canine central nervous system by glial cell transplantation: A model for repair of human myelin disease. *Nat. Med.* 3:54-59.

F. M. Ausubel, R. Brent, R. E. Kingston, D. D. Moore, et al. 1987. Current protocols in molecular biology. John Wiley & Sons, New York.

V. Avellana-Adalid, B. Nait-Oumesmar, F. Lachapelle, A. Baron-Van Evercooren. 1996. Expansion of rat oligodendrocyte progenitors and proliferative "oligospheres" that retain differentiation potential. *J. Neurosci. Res.* 45:558-570.

F. Barany. 1991. Genetic disease detection and DNA amplification using cloned thermostable ligase. *Proc Natl Acad Sci USA.* 88:189-93.

A. L. Calof and D. M. 1989. Analysis of neurogenesis in a mammalian neuroepithelium: Proliferation and differentiation of an olfactory neuron precursor in vitro. *Neuron.* 3:115-127.

A. L. Calof, J. S. Mumm, P. C. Rim, J. Shou. 1998. The neuronal stem cell of the olfactory epithelium. *J. Neurobiol.* 36(2):190-205.

T. Carell, E. A. Wintner, and J. Rebek Jr. 1994a. A novel procedure for the synthesis of libraries containing small organic molecules. *Angewandte Chemie International Edition.* 33:2059-2061.

T. Carell, E. A. Wintner, and J. Rebek Jr. 1994b. A solution phase screening procedure for the isolation of active compounds from a molecular library. *Angewandte Chemie International Edition.* 33:2061-2064.

M. E. Case, M. Schweizer, S. R. Kushner, and N. H. Giles. 1979. Efficient transformation of *Neurospora crassa* by utilizing hybrid plasmid DNA. *Proc Natl Acad Sci USA.* 76:5259-63.

C. Y. Cho, E. J. Moran, S. R. Chemy, J. C. Stephans, et al. 1993. An unnatural biopolymer. *Science.* 261:1303-5.

R. G. Cotton. 1993. Current methods of mutation detection. *Mutat Res.* 285:125-44.

M. T. Cronin, R. V. Fucini, S. M. Kim, R. S. Masino, et al. 1996. Cystic fibrosis mutation detection by hybridization to light-generated DNA probe arrays. *Hum Mutat.* 7:244-55.

M. G. Cull, J. F. Miller, and P. J. Schatz. 1992. Screening for receptor ligands using large libraries of peptides linked to the C terminus of the lac repressor. *Proc Natl Acad Sci USA.* 89:1865-9.

S. E. Cwirla, E. A. Peters, R. W. Barrett, and W. J. Dower. 1990. Peptides on phage: a vast library of peptides for identifying ligands. *Proc Natl Acad Sci USA.*

L. de Louvencourt, H. Fukuhara, H. Heslot, and M. Wesolowski. 1983. Transformation of *Kluyveromyces lactis* by killer plasmid DNA. *J. Bacteriol.* 154:737-42.

J. J. Devlin, L. C. Panganiban, and P. E. Devlin. 1990. Random peptide libraries: a source of specific protein binding molecules. *Science.* 249:404-6.

S. H. DeWitt, J. S. Kiely, C. J. Stankovic, M. C. Schroeder, et al. 1993. "Diversomers": an approach to nonpeptide, nonoligomeric chemical diversity. *Proc Natl Acad Sci USA.* 90:6909-13.

R. Doucette. 1995. Olfactory ensheating cells: Potential for glial cell transplantation into areas of CNS injury. *Histol. Histopathol.* 10:503-507.

F. Felici, L. Castagnoli, A. Musacchio, R. Jappelli, et al. 1991. Selection of antibody ligands from a large library of oligopeptides expressed on a multivalent exposition vector. *J Mol Biol.* 222:301-10.

F. Feron, A. Mackay-Sim, J. L. Andrieu, I. Matthaei, A. Holley, G. Sicard. 1999. Stress induces neurogenesis in nonneuronal cell cultures of adult olfactory epithelium. *Neuroscience.* 88:571-583.

A. Fieck, D. L. Wyborski, and J. M. Short. 1992. Modifications of the *E. coli* Lac repressor for expression in eukaryotic cells: effects of nuclear signal sequences on protein activity and nuclear accumulation. *Nucleic Acids Res.* 20:1785-91.

R. Fleer, P. Yeh, N. Amellal, I. Maury, et al. 1991. Stable multicopy vectors for high-level secretion of recombinant human serum albumin by *Kluyveromyces* yeasts. *Biotechnology (NY).* 9:968-75.

S. P. Fodor, R. P. Rava, X. C. Huang, A. C. Pease, et al. 1993. Multiplexed biochemical assays with biological chips. *Nature.* 364:555-6.

M. A. Gallop, R. W. Barrett, W. J. Dower, S. P. Fodor, et al. 1994. Applications of combinatorial technologies to drug discovery. 1. Background and peptide combinatorial libraries. *J Med Chem.* 37:1233-51.

P. Gasparini, A. Bonizzato, M. Dognini, and P. F. Pignatti. 1992. Restriction site generating-polymerase chain reaction (RG-PCR) for the probeless detection of hidden genetic variation: application to the study of some common cystic fibrosis mutations. *Mol Cell Probes.* 6:1-7.

R. A. Gibbs, P. N. Nguyen, and C. T. Caskey. 1989. Detection of single DNA base differences by competitive oligonucleotide priming. *Nucleic Acids Res.* 17:2437-48.

A. Gritti, E. A. Parati, L. Cova, P. Frolichsthal, R. Galli, E. Wanke, L. Faravelli, D. J. Morassutti, F. Roisen, D. D. Nickel, A. L. Vescovi. 1996. Multipotential stem cells from the adult mouse brain proliferate and self-renew in response to basic fibroblast growth factor. *J. Neurosci.* 16:1091-1100.

M. Grompe, D. M. Muzny, and C. T. Caskey. 1989. Scanning detection of mutations in human ornithine transcarbamoylase by chemical mismatch cleavage. *Proc Natl Acad Sci USA.* 86:5888-92.

E. Harlow and D. Lane. 1988. Antibodies: A laboratory manual. Cold Spring Harbor Laboratory Press, Cold Spring Harbor, N.Y. 726 pp.

E. Harlow, and D. Lane. 1999. Using antibodies: A laboratory manual. Cold Spring Harbor Laboratory Press, Cold Spring Harbor, N.Y.

K. Hayashi. 1992. PCR-SSCP: A method for detection of mutations. *Genetic and Analytical Techniques Applications.* 9:73-79.

R. A. Houghten, J. R. Appel, S. E. Blondelle, J. H. Cuervo, et al. 1992. The use of synthetic peptide combinatorial libraries for the identification of bioactive peptides. *Biotechniques.* 13:412-21.

I. C. Hsu, Q. Yang, M. W. Kahng, and J. F. Xu. 1994. Detection of DNA point mutations with DNA mismatch repair enzymes. *Carcinogenesis.* 15:1657-62.

A. J. Kalyani, D. Piper, T. Mujatba, M. T. Lucero, M. S. Rao. 1998. Spinal cord neuronal precursors generate multiple neuronal phenotypes in culture. *J. Neurosci.* 18(19):7856-7868.

J. Keen, D. Lester, C. Inglehearn, A. Curtis, et al. 1991. Rapid detection of single base mismatches as heteroduplexes on Hydrolink gels. *Trends Genet.* 7:5.

J. M. Kelly and M. J. Hynes. 1985. Transformation of *Aspergillus niger* by the amdS gene of *Aspergillus nidulans*. *Embo J.* 4:475-9.

M. J. Kozal, N. Shah, N. Shen, R. Yang, et al. 1996. Extensive polymorphisms observed in HIV-1 Clade B protease gene using high-density oligonucleotide arrays. *Nat. Med.* 2:753-9.

V. G. Kukekov, E. D. Laywell, O. Suslov, K. Davies, B. Scheffler, L. B. Thomas, T. F. O'Brien, M. Kusakabe, D. A. Steindler. 1999. Multipotent stem/progenitor cells with similar properties arise from two neurogenic regions of adult human brain. *Exp. Neurol.* 156:333-344.

R. C. Ladner, S. K. Guterman, B. L. Roberts, W. Markland, et al. U.S. Pat. No. 5,223,409. 1993. Directed evolution of novel binding proteins.

K. S. Lam, S. E. Salmon, E. M. Hersh, V. J. Hruby, et al. 1991. General method for rapid synthesis of multicomponent peptide mixtures. *Nature.* 354:82-84.

E. D. Laywell, V. G. Kukekov, D. A. Steindler. 1999. Multipotent neurospheres can be derived from forebrain subependymal zone and spinal cord of adult mice after protracted postmortem intervals. *Exp. Neurol.* 156:430-433.

Y. Li, P. M. Field, G. Raisman. 1997. Repair of adult rat corticospinal tracts by transplants of olfactory ensheathing cells. *Science.* 277:2000-2002.

N. Liu, C. B. Shields, F. J. Roisen. 1998. Primary culture of adult mouse olfactory receptor neurons. *Exp. Neurol.* 151:173-183.

K. P. A. MacDonald, W. G. Murrell, P. Bartlett, G. R. Bushell, A. Mackay-Sim. 1996. FGF2 promotes neuronal differentiation in explant cultures of adult and embryonic mouse olfactory epithelium. *J. Neurosci. Res.* 44:27-39.

N. K. Mahanthappa and G. A. Schwarting. 1993. Peptide growth factor control of olfactory neurogenesis and neuron survival in vitro: Roles of EFG and TGF-beta's. *Neuron.* 10:293-305.

J. K. McEntire and S. K. Pixley. 2000. Olfactory receptor neurons in partially purified epithelial cell cultures Comparison of techniques for partial purification and identification of insulin as an important survival factor. *Chem. Senses.* 25:93-101.

R. MacKay. 1997. Stem cells in the central nervous system. *Science.* 276:66-71.

P. Modrich, S.-S. Su, K. G. Au, and R. S. Lahue. U.S. Pat. No. 5,459,039. 1995. Methods for mapping genetic mutations.

T. Mujaba, M. Mayer-Proschel, M. S. Rao. 1998. A common neural progenitor for the CNS and PNS. *Dev. Biol.* 200:1-15.

W. Murrell, G. R. Bushell, J. Livesey, J. McGrath, K. P. A. Mac-Donald, P. R. Bates, A. Mackay-Sim. 1996: Neurogenesis in adult human. *NeuroReport.* 7:1189-1194.

R. M. Myers, Z. Larin, and T. Maniatis. 1985. Detection of single base substitutions by ribonuclease cleavage at mismatches in RNA:DNA duplexes. *Science.* 230:1242-6.

M. K. Njenga and M. Rodriguez. 1996. Animal models of demyelination. *Curr. Opin. Neurol.* 9:1164-1519.

S. K. Pixley. 1992. CNS glial cells support in vitro survival, division, and differentiation of dissociated olfactory neuronal progenitor cells. *Neuron.* 8:1191-1204.

M. Orita, H. Iwahana, H. Kanazawa, K. Hayashi, et al. 1989. Detection of polymorphisms of human DNA by gel electrophoresis as single-strand conformation polymorphisms. *Proc Natl Acad Sci USA.* 86:2766-70.

S. K. Pixley. 1992. Purified cultures of keratin-positive olfactory epithelial cells: Identification of a subset as neuronal supporting (sustentacular) cells. *J. Neurosci. Res.* 31:693-707.

S. K. Pixley, M. Bage, D. Miller, M. L. Miller, M. Shi, L. Hastings. 1994. Olfactory neurons in vitro show phenotypic orientation in epithelial spheres. *NeuroReport.* 5:543-548.

J. Prosser. 1993. Detecting single-base mutations. *Trends Biotechnol.* 11:238-46.

A. Ramon-Cueto, G. W. Plant, J. Avila, M. B. Bunge. 1998. Long-distance axonal regeneration in the transected adult rat spinal cord is promoted by olfactory ensheathing glia transplants. *J. Neurosci.* 18(10):3808-3815.

M. S. Rao, M. Noble, M. Mayer-Proschel. 1998. A tripotential glial precursor cell is present in the developing spinal cord. *Proc. Natl. Acad. Sci. USA.* 95:3996-4001.

B. J. Rossiter and C. T. Caskey. 1990. Molecular scanning methods of mutation detection. *J Biol Chem.* 265:12753-6.

R. K. Saiki, T. L. Bugawan, G. T. Horn, K. B. Mullis, et al. 1986. Analysis of enzymatically amplified beta-globin and HLA-DQ alpha DNA with allele-specific oligonucleotide probes. *Nature.* 324:163-6.

R. K. Saiki, P. S. Walsh, C. H. Levenson, and H. A. Erlich. 1989. Genetic analysis of amplified DNA with immobilized sequence-specific oligonucleotide probes. *Proc Natl Acad Sci USA.* 86:6230-4.

J. A. Saleeba and R. G. Cotton. 1993. Chemical cleavage of mismatch to detect mutations. *Methods Enzymol.* 217:286-95.

M. Satoh and M. Takeuchi. 1995. Induction of NCAM expression in mouse olfactory keratin-positive basal cells in vitro. *Brain Res.* 87:111-119.

J. K. Scott and G. P. Smith. 1990. Searching for peptide ligands with an epitope library. *Science.* 249:386-90.

R. Schade, C. Staak, C. Hendriksen, M. Erhard, et. al. 1996. The production of avian (egg yolk) antibodies IgY. The report and recommendations of ECVAM workshop. *Alternatives to Laboratory Animals (ATLA).* 24:925-934.

L. S. Shihabuddin, J. Ray, F. H. Gage. 1997. FGF2 is sufficient to isolate progenitors found in the adult mammalian spinal cord. *Exp. Neurol.* 148:577-586.

J. S. Sosnowski, M. Gupta, K. H. Reid, F. J. Roisen. 1995. Chemical traumatization of adult mouse olfactory epithelium in situ stimulates growth and differentiation of olfactory neurons in vitro. *Brain Res.* 703:37-48.

K. Sreekrishna, R. H. Potenz, J. A. Cruze, W. R. McCombie, et al. 1988. High level expression of heterologous proteins in methylotrophic yeast *Pichia pastoris*. *Basic Microbiol.* 28:265-78.

R. Tennent and M. I. Chuah. 1996. Ultrastructural study of ensheathing cells in early development of olfactory axons. *Dev. Brain Res.* 95:135-139.

J. Tilburn, C. Scazzocchio, G. G. Taylor, J. H. Zabicky-Zissman, et al. 1983. Transformation by integration in *Aspergillus nidulans*. *Gene.* 26:205-21.

A. L. Vescovi, E. A. Parati, A. Gritti, P. Poulin, M. Ferrario, E. Wanke, P. Prolichsthal-Scheoller, L. Cova, M. Arcellan-Panilio, A. Colombo, R. Galli. 1999. Isolation and cloning of multipotential stem cells from the embryonic human CNS and establishment of transplantable human neural stem cell lines by epigenetic stimulation. *Exp. Neurol.* 156:71-83.

B. Wolozin, P. Lesch, R. Lebovits, T. Sunderland. 1993. Olfactory neuroblasts from Alzheimer donors: studies on APP processing and cell regulation. *Biol. Psychiatry.* 34:824-838.

B. Wolozin, T. Sunderlan, B. Zheng, J. Resau, B. Dufy, J. Barker, R. Swerdlow, H. Coon. 1992. Continuous culture of neuronal cells from adult human olfactory epithelium. *J. Mol. Neurosci.* 3:137-146.

D. L. Wyborski, L. C. DuCoeur, and J. M. Short. 1996. Parameters affecting the use of the lac repressor system in eukaryotic cells and transgenic animals. *Environ Mol Mutagen.* 28:447-58.

D. L. Wyborski, and J. M. Short. 1991. Analysis of inducers of the *E. coli* lac repressor system in mammalian cells and whole animals. *Nucleic Acids Res.* 19:4647-53.

M. M. Yelton, J. E. Hamer, and W. E. Timberlake. 1984. Transformation of *Aspergillus nidulans* by using a trpC plasmid. *Proc Natl Acad Sci USA.* 81:1470-4.

S. C. Zhang, C. Lundberg, D. Lipsitz, L. T. O'Connor, I. D. Duncan. 1998a. Generation of oligodendroglial progenitors from neural stem cells. *J. Neurocytol.* 27:475-489.

The invention claimed is:

1. A method for preparing cultured cells from human olfactory neuroepithelium, comprising:
   dispersing adult human tissue comprising olfactory neuroepithelium to form a cell population comprising separated cells;
   culturing said cell population in a culture medium as an adherent cell population to induce formation of a suspended cell population, wherein said suspended cell population comprises neurospheres, wherein said suspended cell population comprises one or more cells that are each immunoreactive for both nestin and beta-tubulin isotype III; and
   subculturing said suspended cell population, wherein said subculturing comprises collecting said suspended cell population comprising neurospheres; dispersing said neurospheres into separated cells; and culturing said separated cells, wherein said suspended cell population doubles every 18-24 hours in Olfactory Epithelial Medium (OEM) at 37° C. in an atmosphere of humidified 5% $CO_2$, wherein said OEM consists of 90% Minimal Essential Medium with Hanks' salts with L-glutamine and 10% FBS; and
   detecting the presence of cells in the suspended cell population that are each immunoreactive for both nestin and beta-tubulin isotype III with antibodies or antigen-binding fragments thereof that bind nestin and beta tubulin isotype III.

2. The method of claim 1, wherein the adult human tissue is from a cadaver.

3. The method of claim 1, wherein the adult human tissue is collected from a living donor.

4. The method of claim 3, wherein the collecting is carried out by endoscopic removal.

5. The method of claim 1, wherein the subculturing is carried out for more than three weeks.

6. The method of claim 1, wherein the subculturing is carried out for more than six weeks.

7. The method of claim 1, wherein said suspended cell population is subculturable for at least 200 passages in said OEM at 37° C. in an atmosphere of humidified 5% $CO_2$.

8. The method of claim 1, further comprising freezing the suspended cell population.

9. A method of treating a neurological disorder, comprising:
   transplanting cells prepared from human olfactory neuroepithelium into a patient, wherein said cells are prepared by a method comprising the steps of:
      collecting human olfactory neuroepithelium tissue from a living donor by endoscopic removal;
      dispersing the human olfactory neuroepithelium tissue to form a cell population comprising separated cells;
      culturing said cell population in a culture medium as an adherent cell population to induce formation of a suspended cell population, wherein said suspended cell population comprises neurospheres, wherein said suspended cell population comprises one or more cells that are each immunoreactive for both nestin and beta-tubulin isotype III; and
      subculturing said suspended cell population, wherein said subculturing comprises collecting said suspended cell population comprising neurospheres; dispersing said neurospheres into separated cells; and culturing said separated cells, wherein said suspended cell population doubles every 18-24 hours in Olfactory Epithelial Medium (OEM) at 37° C. in an atmosphere of humidified 5% $CO_2$, wherein said OEM consists of 90% Minimal Essential Medium with Hanks' salts with L-glutamine and 10% FBS; and
   detecting the presence of cells in the suspended cell population that are each immunoreactive for both nestin and beta-tubulin isotype III with antibodies or antigen-binding fragments thereof that bind nestin and beta tubulin isotype III.

10. The method of claim 9, wherein the neurological disorder is selected from the group consisting of spinal cord injury, Parkinson's disease, amyotrophic lateral sclerosis and multiple sclerosis.

11. The method of claim 9, wherein the patient has a spinal cord injury and the transplanting is into the site of the spinal cord injury.

12. The method of claim 9, wherein the living donor is the patient.

13. The method of claim 9, further comprising contacting the cells prepared from human olfactory neuroepithelium with a differentiation factor prior to said transplanting.

14. The method of claim 13, wherein the differentiation factor is a growth factor.

* * * * *

UNITED STATES PATENT AND TRADEMARK OFFICE
CERTIFICATE OF CORRECTION

PATENT NO. : 7,838,292 B1  
APPLICATION NO. : 10/112658  
DATED : November 23, 2010  
INVENTOR(S) : Fred J. Roisen It is certified that error appears in the above-identified patent and that said Letters Patent is hereby corrected as shown below:

Column 27, line 34 (Claim 1), please delete "and".
Column 27, line 48 (Claim 1), please delete "beta tubulin" and insert --beta-tubulin--, therefor.
Column 28, line 25 (Claim 9), please delete "and".
Column 28, line 39 (Claim 9), please delete "beta tubulin" and insert --beta-tubulin--, therefor.

Signed and Sealed this
Fifteenth Day of March, 2011

David J. Kappos
*Director of the United States Patent and Trademark Office*